US011231373B2

(12) United States Patent
Nose et al.

(10) Patent No.: US 11,231,373 B2
(45) Date of Patent: Jan. 25, 2022

(54) MEASUREMENT METHOD AND MEASUREMENT DEVICE

(71) Applicant: SYSMEX CORPORATION, Kobe (JP)

(72) Inventors: Tomoyuki Nose, Kobe (JP); Yusuke Muda, Kobe (JP); Kanako Nagaoka, Kobe (JP); Noriyuki Narisada, Kobe (JP); Varun Nambigari, Kobe (JP)

(73) Assignee: SYSMEX CORPORATION, Kobe (JP)

( * ) Notice: Subject to any disclaimer, the term of this patent is extended or adjusted under 35 U.S.C. 154(b) by 128 days.

(21) Appl. No.: 16/202,255

(22) Filed: Nov. 28, 2018

(65) Prior Publication Data

US 2019/0162670 A1 May 30, 2019

(30) Foreign Application Priority Data

Nov. 30, 2017 (JP) ............................ JP2017-231149

(51) Int. Cl.

| | |
|---|---|
| ***G01N 33/53*** | (2006.01) |
| ***G01N 21/75*** | (2006.01) |
| ***G01N 21/07*** | (2006.01) |
| ***G01N 35/00*** | (2006.01) |
| ***B01L 3/00*** | (2006.01) |
| ***G01N 1/40*** | (2006.01) |
| ***G01N 33/543*** | (2006.01) |
| ***G01N 35/02*** | (2006.01) |
| *G01N 21/76* | (2006.01) |
| *G01N 21/64* | (2006.01) |
| *B01L 7/00* | (2006.01) |

(52) U.S. Cl.

CPC .......... *G01N 21/75* (2013.01); *B01L 3/50273* (2013.01); *B01L 3/502753* (2013.01); *G01N 1/4077* (2013.01); *G01N 21/07* (2013.01); *G01N 33/54366* (2013.01); *G01N 35/00069* (2013.01); *G01N 35/025* (2013.01); *B01L 7/00* (2013.01); *B01L 2300/0803* (2013.01); *B01L 2300/087* (2013.01); *B01L 2400/0409* (2013.01); *B01L 2400/0688* (2013.01); *G01N 21/76* (2013.01); *G01N 35/0098* (2013.01); *G01N 2021/6439* (2013.01)

(58) Field of Classification Search

CPC ........ G01N 22/75; G01N 21/07; G01N 21/76; G01N 2021/6439; G01N 1/4077; G01N 35/00069; G01N 35/025; G01N 35/0098; G01N 33/54366; B01L 3/50273; B01L 3/502753; B01L 7/00; B01L 2300/087; B01L 2300/0803; B01L 2400/0409; B01L 2400/0688

USPC ........................................................ 435/7.92

See application file for complete search history.

(56) References Cited

U.S. PATENT DOCUMENTS 8,951,417 B2 2/2015 Strohmeier et al.
2004/0224351 A1* 11/2004 Shinohara ............ G01N 35/025 435/6.19
2008/0056949 A1* 3/2008 Lee .................. G01N 33/54366 422/72
2008/0138247 A1 6/2008 Inganas et al.
2010/0297659 A1* 11/2010 Yoo .................. B01L 3/502753 435/6.16
2014/0352410 A1* 12/2014 Esteves Reis ... G01N 35/00069 73/61.44
2017/0343476 A1* 11/2017 Boege ................ G02B 21/0076
2018/0003704 A1* 1/2018 Horii .................. G01N 35/0098
2018/0195938 A1* 7/2018 Lee ........................ G01N 21/64

FOREIGN PATENT DOCUMENTS

| | | | |
|---|---|---|---|
| CN | 101231285 | A | 7/2008 |
| CN | 107796939 | A | 3/2018 |
| EP | 3290116 | A1 | 3/2018 |
| JP | 2009-148735 | A | 7/2009 |
| JP | 2009-257988 | A | 11/2009 |
| JP | 2011-196849 | A | 10/2011 |
| JP | 2012-506027 | A | 3/2012 |
| JP | 2012-68267 | A | 4/2012 |
| JP | 2012-522450 | A | 9/2012 |
| JP | 2014-44049 | A | 3/2014 |
| WO | 2010104292 | A2 | 9/2010 |
| WO | 2010104292 | A3 | 9/2010 |

OTHER PUBLICATIONS

Stuurman et al "Impact of New Camera Technologies on Discoveries in Cell Biology", Biol Bull, 2016, 231(1), 5-13 (Year: 2016).*
Extended European search report dated Mar. 19, 2019 in a counterpart European patent application.
Office Action dated Feb. 2, 2021 in a counterpart Chinese patent application.

(Continued)

*Primary Examiner* — Gary Counts

(74) *Attorney, Agent, or Firm* — Metrolex IP Law Group, PLLC

(57) ABSTRACT

A method according to one or more aspects may be a method of measuring a detection material contained in a sample by using a cartridge including: chambers each capable of housing at least one of the detection material and a reagent; and a path through which the detection material is transferred between the chambers. The method may include: moving at least one of the chambers and the path to a measurement position and an image capturing range by rotating the cartridge about a rotational shaft; measuring the detection material in the measurement position; and capturing an image of a monitoring target comprising at least one of the chambers and the path in the image capturing range.

20 Claims, 19 Drawing Sheets

(56) References Cited

OTHER PUBLICATIONS

Communication pursuant to Article 94(3) EPC dated Aug. 25, 2021 in a counterpart European patent application.

Office Action dated Oct. 27, 2021 in a counterpart Chinese patent application.

* cited by examiner

MEASUREMENT METHOD AND MEASUREMENT DEVICE

CROSS REFERENCE TO RELATED APPLICATIONS

This application claims priority from prior Japanese Patent Application No. 2017-231149 filed with the Japan Patent Office on Nov. 30, 2017, the entire contents of which are incorporated herein by reference.

BACKGROUND

The disclosure relates to a measurement method and a measurement device that each measure a sample by using a cartridge in which a path is formed (refer to U.S. Pat. No. 8,951,417, for example).

U.S. Pat. No. 8,951,417 discloses that a sample is processed by using a disk-shaped rotation body as illustrated in FIG. 29. The rotation body includes chambers 901 and paths 902 connecting the chambers 901. Magnetic particles 903 that support a detection material are disposed in a chamber 901. The magnetic particles 903 in the chamber 901 move to a path 902 when being attracted by magnetic force. When the rotation body is rotated while the magnetic particles 903 are attracted by the magnetic force, the magnetic particles 903 move in the path 902 in the circumferential direction. When the rotation body is rotated at fast speed, the magnetic particles 903 in the path 902 move outward in the radial direction to another chamber 901. In each chamber 901, cleaning processing and reaction with a detection material are performed by a reagent housed in the chamber 901.

As disclosed in U.S. Pat. No. 8,951,417, a detection material contained in a sample can be processed by injecting the sample into a cartridge as a rotation body housing a reagent and then moving the detection material in the cartridge by rotation and magnetic force. Such a sample processing method allows processing necessary for sample measurement to be perform in a small-sized cartridge, and thus is suitable for a small-sized measurement device for what is called PoC (point of care) testing.

Typically in a large-sized measurement device that performs a large amount of sample processing, the accuracy of measurement is guaranteed by measuring a control material for which a sufficient accuracy is guaranteed in advance. However, when sample processing is performed in a cartridge unlike a case of a large-sized measurement device that repeatedly performs measurement processing with an identical device configuration, there are individual variance of a reagent housed in each cartridge and individual variance of the cartridge, and thus the accuracy is not necessarily guaranteed by measuring the control material. Thus, in sample measurement using a cartridge, it needs to be guaranteed that processing is appropriately performed in an individual cartridge.

SUMMARY

A method according to one or more aspects may be a method of measuring a detection material contained in a sample by using a cartridge including: chambers each capable of housing at least one of the detection material and a reagent; and a path through which the detection material is transferred between the chambers. The method may include: moving at least one of the chambers and the path to a measurement position and an image capturing range by rotating the cartridge about a rotational shaft; measuring the detection material in the measurement position; and capturing an image of a monitoring target comprising at least one of the chambers and the path in the image capturing range.

A measurement device according one or more aspects may include: a rotation mechanism that rotates, about a rotational shaft, a cartridge comprising: chambers each capable of housing at least one of a detection material contained in a sample and a reagent; and a path through which the detection material is transferred between the chambers, to move at least one of the chambers and the path to a measurement position and an image capturing range; a measurement unit that measures the detection material in the measurement position; and an image capturing unit that captures an image of a monitoring target comprising at least one of the chambers and the path in the image capturing range.

A method according to one or more aspects may be a method of measuring a detection material contained in a sample by using a cartridge including: chambers each capable of housing at least one of the detection material and a reagent; and a path through which the detection material is transferred between the chambers. The method may include: executing at least part of measurement processing by rotating the cartridge about a rotational shaft; measuring the detection material that is moved to a measurement position by rotating the cartridge about the rotational shaft; and acquiring information on a monitoring target that comprises at least one of the chambers and the path and is moved to a monitoring position by rotating the cartridge about the rotational shaft in the measurement processing.

A measurement device according to one or more aspects may include: a rotation mechanism that executes at least part of measurement processing by rotating, about a rotational shaft, a cartridge including: chambers each capable of housing at least one of a detection material contained in a sample and a reagent; and a path through which the detection material is transferred between the chambers; an information acquisition unit that acquires information on a monitoring target comprising at least one of the chambers and the path; and a measurement unit that measures the detection material moved to a measurement position by rotating the cartridge by the rotation mechanism. The information acquisition unit acquires information on the monitoring target moved to a monitoring position by rotating the cartridge by the rotation mechanism in the measurement processing.

DETAILED DESCRIPTION

Figures 1A, 1B:
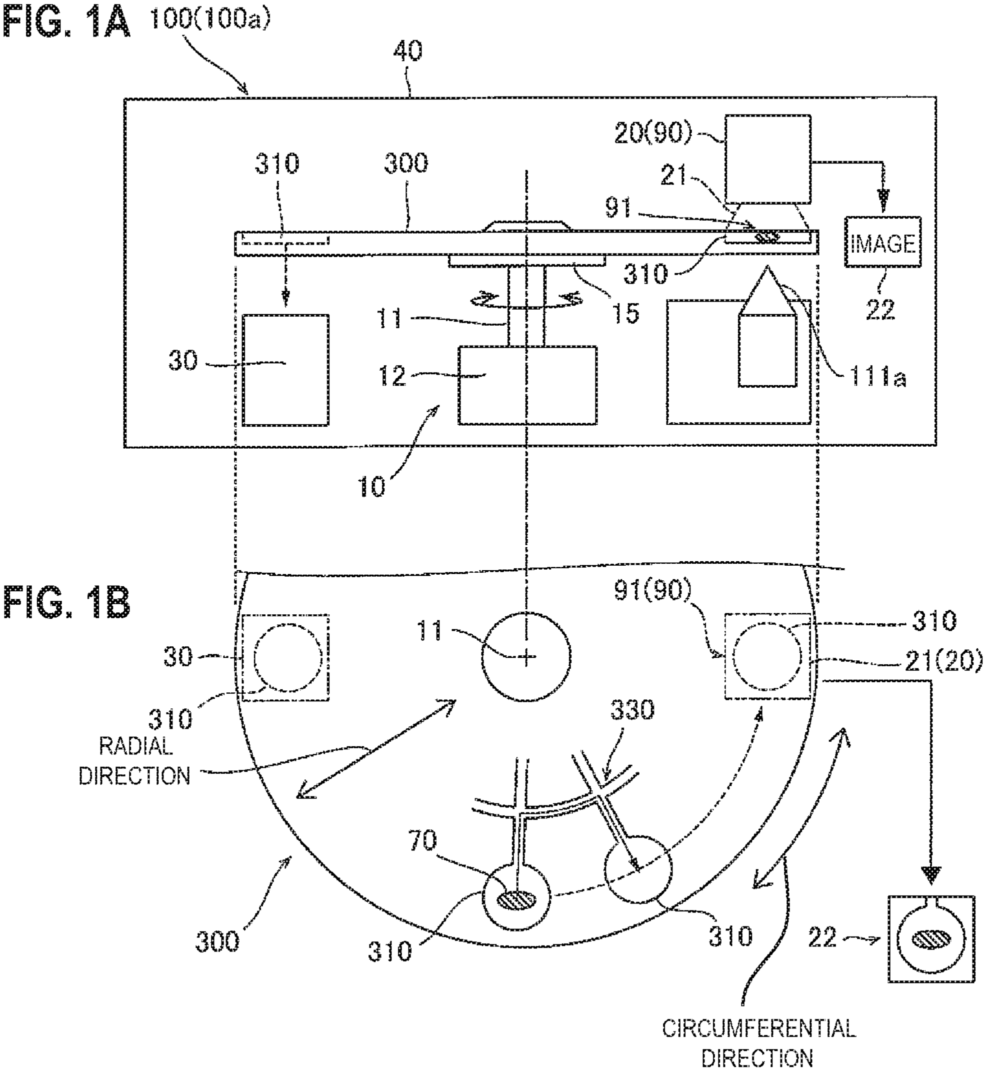
FIG. 1A is a diagram illustrating a schematic side view of a measurement device.
FIG. 1B is a diagram illustrating a schematic plan view of a cartridge.

According to one or more aspects, when sample processing is performed by using a cartridge capable of housing a sample and a reagent, it can be checked whether the processing is appropriately performed in the cartridge.

A measurement method according to a first aspect is a method of measuring a detection material contained in a sample by using a cartridge (300) including chambers (310) each capable of housing at least one of the detection material and a reagent, and a path (330) through which the detection material is transferred between the chambers (310). The method includes: moving at least one of the chambers (310) and the path (330) to a measurement position and an image capturing range (21) by rotating the cartridge (300) about a rotational shaft (11); measuring the detection material in the measurement position; and capturing an image (22) of a monitoring target (MT) including at least one of the chambers (310) and the path (330) in the image capturing range (21).

In the measurement method according to a first aspect, the monitoring target (MT) can be moved into the image capturing range (21) only by rotating the cartridge (300) about the rotational shaft (11), and the image (22) of the monitoring target (MT) can be captured. Thus, in a small-sized measurement device for PoC testing, too, the monitoring target (MT) can be moved to the image capturing range (21) through rotation of the cartridge (300) in a manner same as measurement performed by rotating the chamber (310) of the cartridge (300) to the measurement position. Then, the status of the monitoring target (MT) such as each chamber (310) and the path (330) can be checked based on the image (22) by capturing the image (22) of the monitoring target (MT) moved to the image capturing range (21). As a result, when sample processing is performed by using the cartridge (300) capable of housing a sample and a reagent, it can be checked whether the processing is appropriately performed in the cartridge (300).

In the measurement method according to a first aspect, it may be preferable that, in the measurement of the detection material, light attributable to the detection material moved to the measurement position be measured. The light attributable to the detection material includes, for example, chemiluminescence, fluorescence, and radiation. With this configuration, a measurement result can be easily acquired through optical measurement by rotating the cartridge (300) to move the detection material to the measurement position. The optical measurement can be performed in a non-contact manner by a relatively small-sized light detector, and thus it is possible to reduce increase in the size of a device configuration when an aspect is applied to the small-sized measurement device (100) for PoC testing using the cartridge (300). Thus, the optical measurement may be preferable.

In the measurement method according to a first aspect, it may be preferable that the image (22) captured in a direction facing to a surface of the cartridge (300) and the image capturing range (21) be disposed on a circumferential movement path on which the monitoring target (MT) moves with rotation. With this configuration, the monitoring target (MT) can be reliably positioned in the image capturing range (21) within one rotation of the cartridge (300) without moving the image capturing range (21) relative to the cartridge (300). Accordingly, the image (22) of the monitoring target (MT), which is captured in a direction facing to the monitoring target (MT), allows the status of the monitoring target (MT) to be clearly checked.

In this case, it may be preferable that the image capturing range (21) be a range in which the distance from the rotational shaft (11) is between L1 and L2 inclusive (L2>L1), and the monitoring target (MT) is provided in a range in which the distance from the rotational shaft (11) is between L1 and L2 inclusive in the cartridge (300). With this configuration, it is possible to capture the image (22) in which the monitoring target (MT) is entirely included in the image capturing range (21) at least in a radial direction centered at the rotational shaft (11). Thus, it is possible to capture the image (22) based on which the status of the monitoring target (MT) can be more easily checked.

In the above-described configuration in which the image capturing range (21) is disposed on the circumferential movement path of the monitoring target (MT), it may be preferable that the monitoring targets (MT) be disposed in an arc shape at which the distance from the rotational shaft (11) is substantially equal in the cartridge (300). With this configuration, the monitoring targets (MT) provided at different places can be moved into the image capturing range (21) only by rotating the cartridge (300), and subjected to image capturing. Thus, when there are a plurality of monitoring targets (MT), the image (22) of each monitoring target (MT) can be easily captured without providing a plurality of image capturing ranges (21) nor moving the image capturing range (21).

In the measurement method according to a first aspect, it may be preferable that the image capturing range (21) be fixed at least in measurement processing. With this configuration, it is possible to avoid occurrence of image blur or the like attributable to movement of the image capturing range (21) and thus capture the high-quality image (22) suitable for checking the status of the monitoring target (MT). When the image capturing range (21) is fixed, the monitoring target (MT) can be easily moved to the image capturing range (21) through rotation of the cartridge (300).

In the measurement method according to a first aspect, it may be preferable that the image (22) be captured by an image capturing unit (20) fixed to a lid (102) covering the cartridge (300) and capable of opening and closing. With this configuration, since the image capturing unit (20) is fixed to the lid (102) unlike a configuration in which the image capturing unit is movable, the image (22) of the monitoring target (MT) can be captured with a space-saving configuration sufficiently housed in a small-sized measurement device for PoC testing.

In the measurement method according to a first aspect, it may be preferable that the chambers (310) include a first chamber (CM1) in which the detection material and the reagent are mixed, and a second chamber (CM2) to which a carrier of the detection material is transferred from the first chamber (CM1) through the path (330), and the monitoring target (MT) includes the first chamber (CM1) and the path (330). With this configuration, it is possible to check based on the image (22) of the first chamber (CM1) and the path (330) whether the mixing of the detection material and the reagent is sufficiently performed and whether processing of transferring the carrier of the detection material to the second chamber (CM2) is appropriately performed.

In this case, it may be preferable that information on at least one of the amount of the sample in the first chamber (CM1) and the amount of the reagent in the first chamber (CM1) be acquired based on the area of liquid in the image (22) of the first chamber (CM1). The volume of the first chamber (CM1) is known, and thus it is possible to determine in advance the area of liquid when an appropriate amount of liquid is housed in the first chamber (CM1). With the above-described configuration, information on the amount of liquid in the first chamber (CM1) can be acquired based on the area of liquid in the image (22). As a result, the measurement processing can be performed while it is checked whether the sample and the reagent in appropriate amounts necessary for achieving a certain accuracy of measurement are correctly housed in the first chamber (CM1).

In the above-described configuration in which the monitoring target (MT) includes the first chamber (CM1) and the path (330), it may be preferable that the detection material and the reagent be agitated in the first chamber (CM1) through rotation of the cartridge (300), and information on the uniformity of mixing of the detection material and the reagent is acquired based on grayscale of the image (22) of the first chamber (CM1). With this configuration, as the detection material and the reagent are more sufficiently uniformly mixed, liquid parts in the image have more uniform colors. When the mixing is insufficiency, grayscale variance occurs in the colors of the liquid parts. Thus, the information on the uniformity of mixing of the detection material and the reagent can be acquired based on grayscale variance between pixels in the image (22). As a result, the measurement processing can be performed while it is checked whether the detection material and the reagent are sufficiently uniformly mixed enough to achieve a certain accuracy of measurement.

In the above-described configuration in which the chambers (310) include the first chamber (CM1) and the second chamber (CM2), it may be preferable that the monitoring target (MT) include the first chamber (CM1) and the second chamber (CM2), and information on the amount of carriers transferred from the first chamber (CM1) to the second chamber (CM2) is acquired based on grayscale of the carriers carrying the detection material in the image (22) of each of the first chamber (CM1) and the second chamber (CM2). With this configuration, information on whether the amount of carriers has decreased through the transfer can be acquired based on whether the color concentration of the carriers in the image of the second chamber (CM2) after the transfer has decreased as compared to the color concentration of the carriers in the image of the first chamber (CM1) before the transfer. As a result, the measurement processing can be performed by checking whether the transfer is appropriately performed without remaining of the detection material in the chamber (310) and the path (330) in the measurement processing.

In the measurement method according to a first aspect, it may be preferable that the chambers (310) include a third chamber (311) in which the supplied sample is housed, and the monitoring target (MT) includes the third chamber (311). With this configuration, the measurement processing can be performed after it is checked whether the amount and property of the sample injected into the cartridge (300) are appropriate by capturing the image (22) of a state in which the sample collected from a subject is housed in the third chamber (311).

In the measurement method according to a first aspect, it may be preferable that the cartridge (300) be rotated to separate a liquid component and a solid component contained in the sample in the third chamber (311), and information on at least one of the state of separation and the amount of the solid component is acquired based on the area of the solid component in the image (22) of the third chamber (311). With this configuration, measurement can be performed without a specimen prepared by separating components in the sample in advance by, for example, centrifugation. It is also possible to acquire the information on the state of separation indicating whether the region of the liquid component and the region of the solid component are clearly separated from each other in the image of the third chamber (311). Information on the amount of the solid component can be acquired based on the area of the region of the solid component for the known volume of the third chamber (311). As a result, the measurement processing can be performed after it is checked based on the obtained information whether the separation processing is appropriately performed.

In the above-described, configuration in which the chambers (310) include the third chamber (311), it may be preferable that the chambers (310) include a fourth chamber (312) in which an excessive amount of the sample left after a certain amount of the sample is housed in the third chamber (311) is housed, the monitoring target (MT) includes the fourth chamber (312), and information on the presence of the sample in the fourth chamber (312) is acquired based on the image (22) of the fourth chamber (312). With this configuration, information on whether a certain amount of the sample is reliably housed in the third chamber (311) can be acquired based on the presence of the sample in the fourth chamber (312). As a result, the measurement processing can be performed after it is checked whether the sample in a sufficient amount necessary for achieving a certain accuracy of measurement is injected into the cartridge (300).

In the above-described configuration in which the information is acquired, it may be preferable that outputting of a measurement result obtained by measuring the detection material be controlled based on the acquired information. With this configuration, a user does not need to monitor the process of the measurement processing based on the image (22), but, for example, control can be performed to avoid outputting of the measurement result when the acquired information illustrates occurrence of anomaly in the measurement processing. In this case, outputting of the measurement result is avoided when a sufficient measurement accuracy cannot be achieved due to the occurred anomaly.

In this case, it may be preferable that, when the acquired information indicates anomaly: measurement processing is stopped without outputting a measurement result; a measurement result is output with additional information indicating the occurrence of anomaly; or a measurement result is corrected and output. With this configuration, a measurement result at low reliability can be reliably avoided from being provided to the user by stopping the measurement processing when the acquired information indicates anomaly. When the acquired information indicates anomaly, the measurement result is output with additional information indicating the occurrence of anomaly, and thus the measurement result can be provided to a user while the user knows that the measurement result has low reliability. In a case of anomaly with which a sufficient accuracy can be obtained for a measurement result by correction, the measurement result is corrected and output when the anomaly has occurred so that an appropriate measurement result can be provided to the user despite of the occurrence of anomaly.

In the measurement method according to a first aspect, it may be preferable that the cartridge (300) include an identifier (400) from which information is read by image capturing, the identifier (400) is moved into the image capturing range (21) through rotation of the cartridge (300), and the information recorded in the identifier (400) is read by capturing the image (22) of the identifier (400). With this configuration, information used to perform the measurement processing can be read through image capturing of the monitoring target (MT) and image capturing of the identifier (400) only by rotating the cartridge (300).

In this case, it may be preferable that the identifier (400) include at least one of information that specifies a measurement item measurable by using the cartridge (300), information on the reagent housed in the cartridge (300), and information specifies that the cartridge (300). With this configuration, when there are kinds of cartridges (300) of different measurement items, the information that specifies a measurement item can be used to specify a measurement item and perform processing in accordance with the measurement item. For example, when the expiration date of the reagent is acquired as the information on the reagent, whether the expiration date is passed can be checked. The information that specifies the cartridge (300) enables individual management of the cartridge (300) used in measurement. Thus, for example, the number of times of use may be counted to avoid wrong reuse of the cartridge (300) used a number of times exceeding an allowable number of times of use.

In the measurement method according to a first aspect, it may be preferable that the monitoring targets (MT) be moved into the identical image capturing range (21) by rotating the cartridge (300), and the image (22) including the monitoring targets (MT) is captured. With this configuration, the states of the monitoring targets (MT) can be collectively checked. For example, the status of transfer of the detection material from the chamber (310) to the path (330) can be easily checked by performing image capturing of the chamber (310) and the path (330) connected with the chamber (310).

In the measurement method according to a first aspect, it may be preferable that the detection material contained in the sample be a composite body with magnetic particles (70). With this configuration, the detection material can be transferred between the chambers (310) through the path (330) by attracting the magnetic particles by magnetic force. As a result, the detection material can be transferred in an optional direction in the cartridge (300) through combination of attraction of the magnetic particles by the magnetic force and rotation of the cartridge (300), which facilitates transfer of the detection material.

In this case, it may be preferable that the magnetic particles (70) be collected by a magnet (111*a*) disposed at a position under the image capturing range (21), and the image (22) of the monitoring target (MT) is captured from a side opposite to the magnet (111*a*) with respect to the cartridge (300). With this configuration, since the image capturing is performed from the side opposite to the magnet (111*a*), the magnet (111*a*) is not photographed in the image (22) while the magnetic particles (70) are collected by the magnet (111*a*), and thus the image (22) including all collected magnetic particles (70) can be captured. Accordingly, whether the magnetic particles (70) are appropriately collected can be easily checked based on the image (22).

In the measurement method according to a first aspect, it may be preferable that in the course of measurement processing including processes to be performed in a serial order, each process on each monitoring target (MT) and acquisition of the image (22) of the monitoring target (MT) be simultaneously or alternately performed. With this configuration, the series of processing can be sequentially executed while it is checked based on the image (22) whether the processes to be performed in a serial order are each appropriately performed. Thus, when complicate measurement processing that involves processes is performed in the cartridge (300), the accuracy of the entire measurement processing can be maintained by checking the validity of each process.

In the measurement method according to a first aspect, it may be preferable that at least part of the measurement processing be executed by rotating the cartridge (300) about the rotational shaft (11). With this configuration, not only the movement to the measurement position and the movement to the image capturing range (21) but also at least part of the measurement processing can be executed only by rotating the cartridge (300) about the rotational shaft (11) by using the common rotation mechanism (10).

In the measurement method according to a first aspect, it may be preferable that the cartridge (300) include a housing unit (341) housing a reagent for one measurement of the detection material. The cartridges (300) thus configured house different reagents for one-time use, and thus quality control of the individual cartridges (300) cannot be collectively performed by measuring a control material. Thus, since it can be checked whether processing is appropriately performed in the cartridge (300) based on the image (22) of the monitoring target (MT), an aspect is useful particularly for quality control of measurement using the cartridge (300) including the housing unit (341) housing the reagent for one measurement.

A measurement device (100) according to a second aspect includes: a rotation mechanism (10) that rotates, about a rotational shaft (11), a cartridge (300) including chambers (310) each capable of housing at least one of a detection material contained in a sample and a reagent, and a path (330) through which the detection material is transferred between the chambers (310), to move at least one of the chambers (310) and the path (330) to a measurement position and an image capturing range (21); a measurement unit (30) that measures the detection material in the measurement position; and an image capturing unit (20) that captures an image (22) of a monitoring target (MT) including at least one of the chambers (310) and the path (330) in the image capturing range (21).

In the measurement device (100) according to a second aspect, the monitoring target (MT) can be moved to the image capturing range (21) only by rotating the cartridge (300) about the rotational shaft (11) through the rotation mechanism (10), and the image (22) of the monitoring target (MT) can be captured. Thus, in a small-sized measurement device for PoC testing, too, the monitoring target (MT) can be moved to the image capturing range (21) through rotation of the cartridge (300) in a manner same as measurement performed by rotating each chamber (310) of the cartridge (300) to the measurement position. Then, the status of the monitoring target (MT) such as each chamber (310) and the path (330) can be checked based on the image (22) by capturing the image (22) of the monitoring target (MT) moved to the image capturing range (21) through the image capturing unit (20). As a result, when sample processing is performed by using the cartridge (300) capable of housing a sample and a reagent, it can be checked whether the processing is appropriately performed in the cartridge (300).

In the above-described measurement device according to a second aspect, it may be preferable that the measurement unit (30) include a light detector (31) that detects or measures light attributable to the detection material moved to the measurement position. With this configuration, a measurement result can be easily acquired through optical measurement by rotating the cartridge (300) to move the detection material to the measurement position. The optical measurement can be performed in a non-contact manner by the small-sized light detector (31), and thus it is possible to reduce increase in the size of a device configuration when an aspect is applied to the small-sized measurement device (100) for PoC testing using the cartridge (300). Thus, the optical measurement may be preferable.

In the above-described measurement device according to a second aspect, it may be preferable that the image capturing unit (20) be provided at a position facing to a surface of the cartridge (300), and the image capturing range (21) is disposed on a circumferential movement path on which the monitoring target (MT) moves with by rotation. With this configuration, the monitoring target (MT) can be reliably positioned in the image capturing range (21) within one rotation of the cartridge (300) without moving the image capturing range (21) relative to the cartridge (300). Accordingly, the image (22) of the monitoring target (MT), which is captured in a direction facing to the monitoring target (MT), allows the status of the monitoring target (MT) to be clearly checked.

In this case, it may be preferable that the image capturing range (21) be set to be a range in which the distance from the rotational shaft (11) is between L1 and L2 inclusive to include the monitoring target (MT) provided in a range in which the distance from the rotational shaft (11) is between L1 and L2 inclusive (L2>L1) in the cartridge (300). With this configuration, it is possible to capture the image (22) in which the monitoring target (MT) is entirely included in the image capturing range (21) at least in the radial direction. Thus, it is possible to capture the image (22) based on which the status of the monitoring target (MT) can be more easily checked.

In the above-described configuration in which the image capturing range (21) is disposed on the circumferential movement path of the monitoring target (MT), it may be preferable that the image capturing range (21) be disposed on the movement paths of the monitoring targets (MT) disposed in an arc shape at which the distance from the rotational shaft (11) is substantially equal in the cartridge (300). With this configuration, the monitoring targets (MT) provided at different places can be moved into the image capturing range (21) only by rotating the cartridge (300), and subjected to image capturing. Thus, when there are a plurality of monitoring targets (MT), the image (22) of each monitoring target (MT) can be easily captured without providing a plurality of image capturing units (20) nor moving the image capturing unit (20).

In the above-described measurement device according to a second aspect, it may be preferable that the image capturing unit (20) be fixed at least in measurement processing. With this configuration, it is possible to avoid occurrence of image blur or the like attributable to movement of the image capturing unit (20), and thus capture the high-quality image (22) suitable for checking the status of the monitoring target (MT). When the image capturing unit (20) is fixed, the monitoring target (MT) can be easily moved to the image capturing range (21) through rotation of the cartridge (300).

In the above-described measurement device according to a second aspect, it may be preferable that the image capturing unit (20) be fixed to a lid (102) covering the cartridge (300) and capable of opening and closing. With this configuration, since the image capturing unit (20) is fixed to the lid (102) unlike a configuration in which the image capturing unit is movable, the image (22) of the monitoring target (MT) can be captured with a space-saving configuration sufficiently housed in a small-sized measurement device for PoC testing.

In the above-described measurement device according to a second aspect, it may be preferable that the chambers (310) include a first chamber (CM1) in which the detection material and the reagent are mixed, and a second chamber (CM2) to which the detection material is transferred from the first chamber (CM1) through the path (330), and the monitoring target (MT) includes the first chamber (CM1) and the path (330). With this configuration, it is possible to check based on the image (22) of the first chamber (CM1) and the path (330) whether the mixing of the detection material and the reagent is sufficiently performed and whether processing of transferring the carrier of the detection material to the second chamber (CM2) is appropriately performed.

In the above-described measurement device according to a second aspect, it may be preferable that the chambers (310) include a third chamber (311) in which the supplied sample is housed, and the monitoring target (MT) includes the third chamber (311). With this configuration, the measurement processing can be performed after it is checked whether the amount and property of the sample injected into the cartridge (300) are appropriate by capturing the image (22) of a state in which the sample collected from a subject is housed in the third chamber (311).

In the above-described measurement device according to a second aspect, it may be preferable that the rotation mechanism (10) move, to the image capturing range (21) through rotation of the cartridge (300), an identifier (400) that is provided to the cartridge (300) and from which information is read by image capturing, and the image capturing unit (20) reads the information recorded in the identifier (400) by capturing the image (22) of the identifier (400). With this configuration, information used to perform the measurement processing can be read through image capturing of the monitoring target (MT) and image capturing of the identifier (400) only by rotating the cartridge (300).

In this case, it may be preferable that the identifier (400) include at least one of information that specifies a measurement item measurable by using the cartridge (300), information on the reagent housed in the cartridge (300), and information specifies that the cartridge (300). With this configuration, when there are kinds of cartridges (300) of different measurement items, the information that specifies a measurement item can be used to specify a measurement item and perform processing in accordance with the measurement item. For example, when the expiration date of the reagent is acquired as the information on the reagent, whether the expiration date is passed can be checked. The information that specifies the cartridge (300) enables individual management of the cartridge (300) used in measurement. Thus, for example, the number of times of use may be counted to avoid wrong reuse of the cartridge (300) used a number of times exceeding an allowable number of times of use.

In the above-described measurement device according to a second aspect, it may be preferable that the rotation mechanism (10) move the monitoring targets (MT) into the identical image capturing range (21) by rotating the cartridge (300), and the image capturing unit (20) capture the image (22) including the monitoring targets (MT). With this configuration, the states of the monitoring targets (MT) can be collectively checked. For example, the status of transfer of the detection material from the chamber (310) to the path (330) can be easily checked by performing image capturing of the chamber (310) and the path (330) connected with the chamber (310).

In the above-described measurement device according to a second aspect, it may be preferable that the detection material contained in the sample be a composite body with magnetic particles (70). With this configuration, the detection material can be transferred between the chambers (310) through the path (330) by attracting the magnetic particles by magnetic force. As a result, the detection material can be transferred in an optional direction in the cartridge (300) through combination of attraction of the magnetic particles by the magnetic force and rotation of the cartridge (300), which facilitates transfer of the detection material.

In this case, it may be preferable that a magnet (111*a*) that is disposed at a position under the image capturing range (21) and collects the magnetic particles (70) be further included, and the image capturing unit (20) be disposed on a side opposite to the magnet (111*a*) with respect to the cartridge (300). With this configuration, since the image capturing is performed from the side opposite to the magnet (111*a*), the magnet (111*a*) is not photographed in the image (22) while the magnetic particles (70) are collected by the magnet (111*a*), and thus the image (22) including all collected magnetic particles (70) can be captured. Accordingly, whether the magnetic particles (70) are appropriately collected can be easily checked based on the image (22).

In the above-described measurement device according to a second aspect, it may be preferable to further include a communication unit (143) that transmits the image (22) obtained by image capturing to an external analysis device (700) and acquires an analysis result. With this configuration, when no analysis unit that performs image analysis is provided due to constraint on the structure of the small-sized measurement device (100) for PoC testing, image analysis can be performed by using the external analysis device (700). Thus, the state of the monitoring target (MT) can be checked based on an analysis result of the image (22) of the monitoring target (MT) when no image analysis is performed by the measurement device (100).

In the above-described measurement device according to a second aspect, it may be preferable to further include an analysis unit (142) that analyzes the image (22) obtained by image capturing. With this configuration, the measurement device (100) can perform image analysis, which eliminates the need to perform communication with an external analysis device or the like to perform image analysis. As a result, a user does not need to prepare communication environment for image analysis, which improves device convenience.

In the above-described configuration in which the analysis unit (142) is included, it may be preferable that the monitoring target (MT) include a first chamber (CM1) in which the detection material and the reagent are mixed, and the analysis unit (142) acquire information on at least one of the amount of the sample in the first chamber (CM1) and the amount of the reagent in the first chamber (CM1) based on the area of liquid in the image (22) of the first chamber (CM1). The volume of the first chamber (CM1) is known, and thus it is possible to determine in advance the area of liquid when an appropriate amount of liquid is housed in the first chamber (CM1). With the above-described configuration, information on the amount of liquid in the first chamber (CM1) can be acquired based on the area of liquid in the image (22). As a result, the measurement processing can be performed while it is checked whether the sample and the reagent in appropriate amounts necessary for achieving a certain accuracy of measurement are correctly housed in the first chamber (CM1).

In the above-described configuration in which the analysis unit (142) is included, it may be preferable that the monitoring target (MT) include a first chamber (CM1) in which the detection material and the reagent are mixed, the rotation mechanism (10) agitate the detection material and the reagent in the first chamber (CM1) through rotation of the cartridge (300), and the analysis unit acquire information on the uniformity of mixing of the detection material and the reagent based on grayscale of the image (22) of the first chamber (CM1). With this configuration, as the detection material and the reagent are more sufficiently uniformly mixed, liquid parts in the image have more uniform colors. When the mixing is insufficiency, grayscale variance occurs in the colors of the liquid parts. Thus, information on the amount of liquid in the first chamber (CM1) can be acquired based on the area of liquid in the image (22). As a result, the measurement processing can be performed while it is checked whether the detection material and the reagent are sufficiently uniformly mixed enough to achieve a certain accuracy of measurement.

In the above-described configuration in which the analysis unit (142) is included, it may be preferable that the monitoring target (MT) include a first chamber (CM1) in which the detection material and the reagent are mixed, and a second chamber (CM2) to which a carrier carrying the detection material is transferred from the first chamber (CM1) through the path (330), and the analysis unit (142) acquire information on the amount of carriers transferred from the first chamber (CM1) to the second chamber (CM2) based on grayscale of the carrier in the image (22) of each of the first chamber (CM1) and the second chamber (CM2). With this configuration, information on whether the amount of carriers has decreased through the transfer can be acquired based on whether the color concentration of the carriers in the image of the second chamber (CM2) after the transfer has decreased as compared to the color concentration of the carriers in the image of the first chamber (CM1) before the transfer. As a result, the measurement processing can be performed by checking whether the transfer is appropriately performed without remaining of the detection material in the chamber (310) and the path (330) in the measurement processing.

In the above-described configuration in which the analysis unit (142) is included, it may be preferable that the monitoring target (MT) include a third chamber (311) in which the sample supplied to the cartridge (300) is housed, the rotation mechanism (10) separates a liquid component and a solid component contained in the sample in the third chamber (311) through rotation of the cartridge (300), and the analysis unit acquire information on at least one of the state of separation and the amount of the solid component based on the area of the solid component in the image (22) of the third chamber (311). With this configuration, measurement can be performed without a specimen prepared by separating components in the sample in advance by, for example, centrifugation. It is also possible to acquire the information on the state of separation indicating whether the region of the liquid component and the region of the solid component are clearly separated from each other in the image of the third chamber (311). Information on the amount of the solid component can be acquired based on the area of the region of the solid component for the known volume of the third chamber (311). As a result, the measurement processing can be performed after it is checked based on the obtained information whether the separation processing is appropriately performed.

In this case, it may be preferable that the monitoring target (MT) include a fourth chamber (312) in which an excessive amount of the sample left after a certain amount of the sample is housed in the third chamber (311) is housed, and the analysis unit (142) acquire information on the presence of the sample in the fourth chamber (312) based on the image (22) of the fourth chamber (312). With this configuration, information on whether a certain amount of the sample is reliably housed in the third chamber (311) can be acquired based on the presence of the sample in the fourth chamber (312). As a result, the measurement processing can be performed after it is checked whether the sample in a sufficient amount necessary for achieving a certain accuracy of measurement is injected into the cartridge (300).

In the above-described configuration in which the analysis unit (142) acquires the information, it may be preferable that a control unit (140) that control, based on the information acquired by the analysis unit (142), outputting of a measurement result obtained by measuring the detection material is further included. With this configuration, a user does not need to monitor the process of the measurement processing based on the image (22), but, for example, control can be performed to avoid outputting of the measurement result when the acquired information illustrates occurrence of anomaly in the measurement processing. In this case, outputting of the measurement result is avoided when a sufficient measurement accuracy cannot be achieved due to the occurred anomaly.

In this case, it may be preferable that, when the acquired information indicates anomaly, the control unit (140) performs control by: stopping measurement processing without outputting a measurement result; outputting a measurement result with additional information indicating the occurrence of anomaly; or correcting and outputting a measurement result. With this configuration, a measurement result at low reliability can be reliably avoided from being provided to the user by stopping the measurement processing when the acquired information indicates anomaly. When the acquired information indicates anomaly, the measurement result is output with additional information indicating the occurrence of anomaly, and thus the measurement result can be provided to a user while the user knows that the measurement result has low reliability. In a case of anomaly with which a sufficient accuracy can be obtained for a measurement result by correction, the measurement result is corrected and output when the anomaly has occurred so that an appropriate measurement result can be provided to the user despite of the occurrence of anomaly.

In the above-described measurement device according to a second aspect, it may be preferable that, in the course of measurement processing including processes to be performed in a serial order, the image capturing unit (20) captures the image (22) of the monitoring target (MT) simultaneously or alternately with each process on each monitoring target (MT). With this configuration, the series of processing can be sequentially executed while it is checked whether the processes to be performed in a serial order are each appropriately performed. Thus, when complicate measurement processing that involves processes is performed in the cartridge (300), the accuracy of the entire measurement processing can be maintained by checking the validity of each process.

In the above-described measurement device according to a second aspect, it may be preferable that the rotation mechanism (10) execute at least part of the measurement processing by rotating the cartridge (300) about the rotational shaft (11). With this configuration, not only the movement to the measurement position and the movement to the image capturing range (21) but also at least part of the measurement processing can be executed only by rotating the cartridge (300) about the rotational shaft (11) by using the common rotation mechanism (10).

A measurement method according to a third aspect is a method of measuring a detection material contained in a sample by using a cartridge (300) including chambers (310) each capable of housing at least one of the detection material and a reagent, and a path (330) through which the detection material is transferred between the chambers (310). The method includes: executing at least part of measurement processing by rotating the cartridge (300) about the rotational shaft (11); measuring the detection material moved to a measurement position by rotating the cartridge (300) about the rotational shaft (11); and acquiring information on a monitoring target (MT) including at least one of the chambers (310) and the path (330) and moved to a monitoring position (91) by rotating the cartridge (300) about the rotational shaft (11) in the measurement processing.

In the measurement method according to a third aspect, the monitoring target (MT) including at least one of the chambers (310) and the path (330) can be moved to the monitoring position (91) by rotating the cartridge (300) about the rotational shaft (11), and information on the monitoring target (MT) moved to the monitoring position (91) can be acquired. Thus, in a small-sized measurement device for PoC testing, too, the monitoring target (MT) can be moved to the monitoring position (91) through rotation of the cartridge (300) in a manner same as part of the measurement processing performed by rotating each chamber (310) and the path (330) of the cartridge (300). Since the information on the monitoring target (MT) moved to the monitoring position (91) is acquired, the status of the monitoring target (MT) such as each chamber (310) and the path (330) can be checked based on the acquired information. As a result, when sample processing is performed by using the cartridge (300) capable of housing a sample and a reagent, it can be checked whether the processing is appropriately performed in the cartridge (300).

A measurement device (100) according to a fourth aspect includes: a rotation mechanism (10) that executes at least part of measurement processing by rotating, about a rotational shaft (11), a cartridge (300) including chambers (310) each capable of housing at least one of a detection material contained in a sample and a reagent, and a path (330) through which the detection material is transferred between the chambers (310); an information acquisition unit (90) that acquires information on a monitoring target (MT) including at least one of the chambers (310) and the path (330); and a measurement unit (30) that measures the detection material moved to a measurement position through rotation of the cartridge (300) by the rotation mechanism (10). The information acquisition unit (90) acquires information on the monitoring target (MT) moved to the monitoring position (91) through rotation of the cartridge (300) by the rotation mechanism (10) in the measurement processing.

In the measurement device (100) according to a fourth aspect, the monitoring target (MT) including at least one of the chambers (310) and the path (330) can be moved to the monitoring position (91) by rotating the cartridge (300) about the rotational shaft (11), and the information on the monitoring target (MT) moved to the monitoring position (91) can be acquired by the information acquisition unit (90). Thus, in a small-sized measurement device for PoC testing, too, the monitoring target (MT) can be moved to the monitoring position (91) through rotation of the cartridge (300) in a manner same as sample processing performed by rotating each chamber (310) and the path (330) of the cartridge (300). Since the information on the monitoring target (MT) moved to the monitoring position (91) is acquired by the information acquisition unit (90), the status of the monitoring target (MT) such as each chamber (310) and the path (330) can be checked based on the acquired information. As a result, when sample processing is performed by using the cartridge (300) capable of housing a sample and a reagent, it can be checked whether the processing is appropriately performed in the cartridge (300).

When sample processing is performed by using a cartridge capable of housing a sample and a reagent, it can be checked whether the processing is appropriately performed in the cartridge.

Embodiments will be described below with reference to the accompanying drawings.

(Outline of Measurement Device)

The following describes outline of a measurement device according to one or more embodiments with reference to FIGS. 1A and 1B.

A measurement device 100 measures a sample injected into a cartridge 300 including chambers 310 each capable of housing at least one of a detection material contained in a sample and a reagent, and a path 330 through which the detection material is transferred between the chambers 310. The measurement device 100 is, for example, a small-sized measurement device for PoC testing, and executes measurement by a simple operation.

The sample is a living body specimen collected from, for example, a human as a subject. The sample may be blood, urine, tissue fluid, or any other body fluid. The sample contains liquid as a primary component, and may contain a solid component such as a cell. The measurement of the sample includes measurement of the presence of the detection material in accordance with a measurement item, the amount and concentration of the detection material, the size and shape thereof when the detection material is a particle, and the like. The kind of the reagent housed in the cartridge 300 differs depending on the measurement item. Kinds of the cartridge 300 may be available for each measurement item. The cartridge 300 may allow measurement of different measurement items.

The cartridge 300 is a replaceable consumable. Specifically, the cartridge 300 is discarded when used for measurement a number of times set in advance. The cartridge 300 can be used once or several times. A cartridge refers to a replaceable component having collection of functions necessary for detection of a detection material contained in a sample.

The cartridge 300 has, for example, a flat plate shape in which a space is formed. The cartridge 300 includes the chambers 310 each capable of housing a detection material contained in a sample and a reagent. The cartridge 300 includes one or a plurality of paths 330 through which the detection material is transferred between the chambers 310. The cartridge 300 is obtained by, for example, laminating a transparent film on the surface of a member through which holes are formed for the chambers 310 and the paths 330 to block opening parts so that internal spaces such as the chambers 310 and the paths 330 are formed. The cartridge 300 allows visual recognition and image capturing of the internal spaces and liquid or the like in the spaces from the outside through the transparent film.

Each chamber 310 may house a reagent in advance, or may house no reagent. A reagent may be injected to the chamber 310 housing no reagent from another place in the cartridge 300 or from the outside of the cartridge 300. Each chamber 310 is a space part having a volume enough to house a predetermined amount of liquid. Each path 330 is a space part extending to connect the chambers 310, and a detection material can be transferred at least through the path 330. The path 330 is, for example, a flow path through which liquid can circulate. The path 330 may be any path through which a detection material contained in a sample can be transferred, but does not necessarily need to be a path through which liquid can circulate.

The measurement device 100 can perform, inside the cartridge 300, mixing of a sample and a reagent, agitation, heating, cooling, movement of solid or liquid containing the sample, and other various kinds of operations.

As illustrated in FIG. 1A, the measurement device 100 includes a rotation mechanism 10, an image capturing unit 20, and a measurement unit 30. The rotation mechanism 10, the image capturing unit 20, and the measurement unit 30 are housed in, for example, a housing 40.

The housing 40 is a box-shaped member including an internal space having a predetermined volume, or is a combination of frames and exterior plates. The housing 40 of the measurement device 100 for PoC testing has a small box shape that allows installation on a table.

The rotation mechanism 10 includes a rotational shaft 11, and a drive unit 12 such as a motor that rotates the rotational shaft 11. The rotation mechanism 10 holds the cartridge 300 through the rotational shaft 11. The rotational shaft 11 points in the vertical direction, for example, when the measurement device 100 is installed. The cartridge 300 is supported in a posture along the horizontal direction by the rotation mechanism 10. A direction of rotation about the rotational shaft 11 in a plane along the surface of the cartridge 300 is defined to be a circumferential direction, and a direction toward or away from the rotational shaft 11 in the plane along the surface of the cartridge 300 is defined to be a radial direction.

The cartridge 300 rotates about the rotational shaft 11 as the drive unit 12 rotates the rotational shaft 11 about the axis thereof. As a result, the chambers 310 and the paths 330 of the cartridge 300 each move in the circumferential direction about the rotational shaft 11 on a circumferential orbit having a rotational radius corresponding to the distance thereof from the rotational shaft 11 in the radial direction.

The rotation mechanism 10 rotates the cartridge 300 about the rotational shaft 11 to move at least one of the chambers 310 and each path 330 to a measurement position and an image capturing range 21.

The rotation mechanism 10 may execute at least part of measurement processing by rotating the cartridge 300 about the rotational shaft 11. Accordingly, not only the movement to the measurement position and the movement to the image capturing range 21 but also at least part of the measurement processing can be executed only by rotating the cartridge 300 about the rotational shaft 11 by using the common rotation mechanism 10.

In the disclosure, the measurement processing is a concept including not only measurement of a detection material but also processing performed on a detection material in the cartridge or a sample containing the detection material to prepare the detection material for the measurement, and is a broad concept that may include a series of processes until the measurement of the detection material is performed.

Specifically, the part of the measurement processing includes, for example, one or a plurality of processing of moving a detection material through rotation of the cartridge 300, processing of performing centrifugation of a liquid component and a solid component through fast rotation of the cartridge 300, and processing of agitating liquid through repetition of acceleration and deceleration of the rotational speed in rotation of the cartridge 300.

The rotation mechanism 10 executes at least part of the measurement processing in cooperation with another mechanism. For example, in the processing of moving a detection material, while the cartridge 300 is rotated, magnetic force is exerted by a magnet 111*a* from the outside of the cartridge 300 to move a magnetic particle formed in a composite body with a detection material in the cartridge 300. In this case, when the magnet 111*a* is moved in the radial direction, the magnetic particle formed in a composite body with the detection material can be moved in an optional direction in the cartridge 300 by combining movement in the circumferential direction by rotation of the cartridge 300 and movement in the radial direction along with the movement of the magnet 111*a*, as illustrated in FIG. 1B.

The image capturing unit 20 captures an image 22 of the cartridge 300. The image capturing unit 20 is, for example, a camera including an image sensor. The image capturing unit 20 is provided in the housing 40 so that the image capturing range 21 is formed on the surface of the cartridge 300 rotated by the rotation mechanism 10. Since the internal spaces of the cartridge 300 can be visually recognized from the outside, the image capturing unit 20 can capture the image 22 of the internal spaces such as the chambers 310 and the paths 330 by performing image capturing through reception of light in a visible light range. Although the image capturing unit 20 is disposed above the cartridge 300 in FIGS. 1A and 1B, the image capturing unit 20 may be disposed below the cartridge 300.

The measurement unit 30 measures a detection material in the measurement position. Specifically, the measurement unit 30 measures the detection material moved to the measurement position through rotation of the cartridge 300 by the rotation mechanism 10. A reagent in the cartridge 300 generates, through reaction with the detection material in a sample, a change that enables direct or indirect measurement of the detection material from the outside of the cartridge 300. For example, the reagent emits light in accordance with the amount of the detection material. The light emission is, for example, chemiluminescence or fluorescence. The reagent contains, for example, a labeling material that differentially connects with the detection material. The labeling material generates, for example, a signal measurable from the outside of the cartridge 300. The labeling material includes a chemiluminescence material, a fluorescent substance, or a radioactive isotope. The reagent may be a material that is colored or clouded in accordance with the amount of the detection material.

The measurement unit 30 directly or indirectly measures a detection material in a sample by detecting a change generated through reaction of the detection material with a reagent. For example, to measure a detection material in a chamber 310 of the cartridge 300 supported by the rotation mechanism 10, the measurement unit 30 is disposed at a position under a movement path of the chamber 310, which is formed by rotation of the cartridge 300. The rotation mechanism 10 rotates the cartridge 300 to move the chamber 310 housing the detection material to the position of measurement by the measurement unit 30. The measurement unit 30 measures the detection material moved to the measurement position.

When performing light emission detection, the measurement unit 30 includes a light detector such as a photomultiplier tube, a photoelectric tube, or a light diode. When performing radiation detection, the measurement unit 30 includes a radiation detector such as a scintillation counter. When performing fluorescence, coloring, or cloud detection, the measurement unit 30 includes a light source and a light receiving element.

The measurement device 100 according to one or more embodiments is capable of monitoring whether a measurement operation is appropriately performed by capturing the image 22 of a monitoring target MT through the image capturing unit 20, the monitoring target MT being at least one of the chambers 310 and each path 330 included in the cartridge 300.

Specifically, the image capturing unit 20 acquires, in the image capturing range 21, the image 22 of the monitoring target MT including at least one of the chambers 310 and each path 330. In this case, the rotation mechanism 10 rotates the cartridge 300 to move the monitoring target MT including at least one of the chambers 310 and each path 330 to the image capturing range 21 of the image capturing unit 20. For example, as illustrated in FIG. 1B, the rotation mechanism 10 rotates the cartridge 300 to move the chamber 310 as the monitoring target MT in the circumferential direction and position the chamber 310 in the image capturing range 21 of the image capturing unit 20. The image capturing unit 20 captures the image 22 in the image capturing range 21. Accordingly, the image 22 of the monitoring target MT is acquired. The image 22 may be acquired as a still image or may be acquired in the format of a moving image.

For example, the acquired image 22 is checked by a user to check whether the measurement operation is appropriately performed or whether anomaly occurs in the measurement processing. For example, the acquired image 22 is provided with image analysis to acquire information on the monitoring target MT, thereby determining whether the measurement operation is appropriately performed or whether anomaly occurs in the measurement processing based on the acquired information without performing check by a user.

In this manner, according to the exemplary configuration illustrated in FIGS. 1A and 1B, the monitoring target MT including at least one of the chambers 310 and each path 330 can be moved to the image capturing range 21 of the image capturing unit 20 only by rotating the cartridge 300, thereby capturing the image 22 of the monitoring target MT. Thus, in a small-sized measurement device for PoC testing, too, the monitoring target MT can be moved to the image capturing range 21 through rotation of the cartridge 300 in a manner same as measurement performed by rotating the chamber 310 of the cartridge 300 to the measurement position. Then, the status of the monitoring target MT such as each chamber 310 or the path 330 can be checked based on the image 22 by acquiring, through the image capturing unit 20, the image 22 of the monitoring target MT moved to the image capturing range 21. As a result, when sample processing is performed by using the cartridge 300 capable of housing a sample and a reagent, whether the processing is appropriately performed in the cartridge 300 can be checked.

Figure 2:
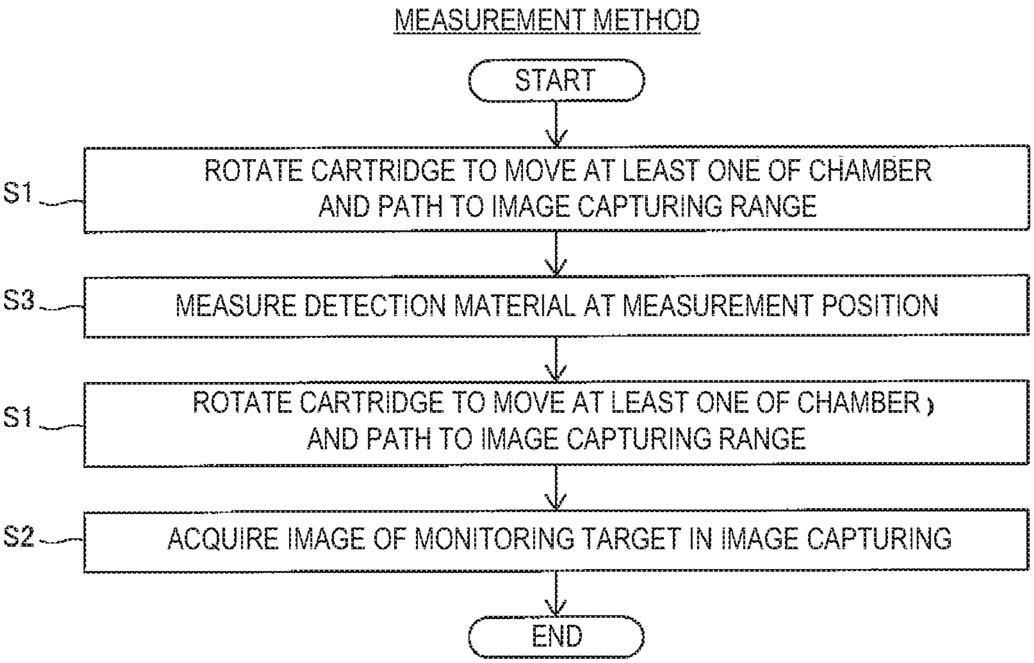
FIG. 2 is a flowchart illustrating a measurement method.

The following describes a measurement method according to one or more embodiments. The measurement method according to one or more embodiments is a method of measuring a detection material contained in a sample by using the cartridge 300 including the chambers 310 each capable of housing at least one of the detection material and a reagent, and a path 330 through which the detection material is transferred between the chambers 310. As illustrated in FIG. 2, the measurement method includes the following steps S1 to S3. (S1) The cartridge 300 is rotated about the rotational shaft 11 to move at least one of the chambers 310 and each path 330 to the measurement position and the image capturing range 21. (S2) The detection material is measured in the measurement position. (S3) The image 22 of the monitoring target MT including at least one of the chambers 310 and each path 330 is acquired in the image capturing range 21.

At step S1, before step S2, the detection material in the cartridge 300 is moved to the measurement position through the rotation of the cartridge 300. Also, at step S1, before step S3, the monitoring target MT such as each chamber 310 or the path 330 is moved to the image capturing range 21 through the rotation of the cartridge 300. In other words, steps S1 to S3 are not necessarily performed in the stated order, and step S1 may be performed a plurality of times as illustrated in FIG. 2. Specifically, step S3 is executed after the monitoring target MT is moves to the image capturing range 21 at step S1, and step S2 is executed after the chamber 310 is moved to the measurement position at step S1.

At step S2, the detection material in the cartridge 300 moved to the measurement position through the rotation of the cartridge 300 is measured by the measurement unit 30.

At step S3, the image 22 of the monitoring target MT positioned in the image capturing range 21 through the rotation of the cartridge 300 is acquired. For example, when the sample and the reagent are mixed in the chamber 310 as the monitoring target MT, step S3 is performed to determine the mixing state of the sample and the reagent in the image 22 of the monitoring target MT. As a result, the acquired image 22 is checked by a user to determine whether the measurement operation is appropriately performed or whether anomaly occurs in the measurement processing. For example, the acquired image 22 is provided with image analysis, thereby determining whether the measurement operation is appropriately performed or whether anomaly occurs in the measurement processing without performing check by a user.

In this manner, according to the measurement method according to one or more embodiments, the monitoring target MT can be positioned in the image capturing range 21 only by rotating the cartridge 300 about the rotational shaft 11. Thus, in a small-sized measurement device for PoC testing, too, the monitoring target MT can be moved to the image capturing range 21 through rotation of the cartridge 300 in a manner same as measurement performed by rotating the chamber 310 of the cartridge 300 to the measurement position. Then, the status of the monitoring target MT such as each chamber 310 or the path 330 can be checked based on the image 22 by capturing the image 22 of the monitoring target MT moved to the image capturing range 21. As a result, when sample processing is performed by using the cartridge 300 capable of housing a sample and a reagent, whether the processing is appropriately performed in the cartridge 300 can be checked.

As described above, at least part of the measurement processing may be executed by rotating the cartridge 300 about the rotational shaft 11. Accordingly, not only the movement to the measurement position and the movement to the image capturing range 21 but also at least part of the measurement processing can be executed only by rotating the cartridge 300 about the rotational shaft 11 by using the common rotation mechanism 10.

(Modification)

In the above-described exemplary configuration, image capturing of the monitoring target MT is performed to allow the status of the monitoring target MT to be checked based on the image 22, but information indicating the status of the monitoring target MT may be acquired by a method other than image capturing.

Specifically, a measurement device **100*a* according to a modification illustrated in FIGS. 1A and 1B includes: the rotation mechanism 10 that executes at least part of the measurement processing by rotating, about the rotational shaft 11, the cartridge 300 including the chambers 310 each capable of housing at least one of a detection material contained in a sample and a reagent, and a path 330 through which the detection material is transferred between the chambers 310; an information acquisition unit 90 that acquires information on the monitoring target MT including at least one of the chambers 310 and each path 330; and the measurement unit 30 that measures the detection material moved to the measurement position through rotation of the cartridge 300 by the rotation mechanism 10. The information acquisition unit 90 acquires information on the monitoring target MT moved to a monitoring position 91 through rotation of the cartridge 300 by the rotation mechanism 10** in the measurement processing.

The information acquisition unit 90 is capable of acquiring information on the monitoring target MT. The monitoring position 91 of the information acquisition unit 90 is same as an image capturing position illustrated in FIGS. 1A and 1B. The information acquisition unit 90 may be, for example, the image capturing unit 20 or a configuration other than the image capturing unit. The information acquisition unit 90 may acquire information on the monitoring target MT by, for example, an optical method, an electric method, or an electromagnetic method. For example, the information acquisition unit 90 may acquire information on transmittancy of the monitoring target MT by irradiating the monitoring target MT such as a chamber 310 with light and acquiring transmitted light and/or scattered light. When magnetic particles exist in the chamber 310, the transmittancy changes in accordance with the concentration of the magnetic particles, and thus the concentration or dispersion state of the magnetic particles can be determined based on the acquired transmittancy. The information acquisition method is set in accordance with information of the monitoring target MT to be acquired. Whether processing is appropriately performed in the cartridge 300 can be checked based on the acquired information.

In this manner, in the measurement device 100*a*, the monitoring target MT can be positioned at the monitoring position 91 only by rotating the cartridge 300 through the rotation mechanism 10. Thus, in a small-sized measurement device for PoC testing, too, the monitoring target MT can be moved to the monitoring position 91 through rotation of the cartridge 300 in a manner same as sample processing performed in each chamber 310 or the path 330 of the cartridge 300 with rotation. Then, information on the monitoring target MT moved to the monitoring position 91 is acquired by the information acquisition unit 90, and thus the status of the monitoring target MT such as each chamber 310 or the path 330 can be checked based on the acquired information. As a result, when sample processing is performed by using the cartridge 300 capable of housing a sample and a reagent, whether the processing is appropriately performed in the cartridge 300 can be checked.

Similarly, a measurement method according to the modification is a method of measuring a detection material contained in a sample by using the cartridge 300 including chambers 310 each capable of housing at least one of the detection material and a reagent, and a path 330 through which the detection material is transferred between the chambers 310. The method includes the following steps. (1*a*) At least part of the measurement processing is executed by rotating the cartridge 300 about the rotational shaft 11. (2*a*) The detection material moved to the measurement position by rotating the cartridge 300 about the rotational shaft 11 is measured. (3*a*) In the measurement processing, information on the monitoring target MT including at least one of the chambers 310 and each path 330 and moved to the monitoring position 91 by rotating the cartridge 300 about the rotational shaft 11 is acquired.

In the measurement method according to the modification, the monitoring target MT can be positioned at the monitoring position 91 only by rotating the cartridge 300 at step (3*a*). Thus, in the small-sized measurement device 100*a* for PoC testing, the monitoring target MT can be moved to the monitoring position 91 through rotation of the cartridge 300 in a manner same as sample processing performed in each chamber 310 or the path 330 of the cartridge 300 with rotation. Then, information on the monitoring target MT moved to the monitoring position 91 is acquired, and thus the status of the monitoring target MT such as each chamber 310 or the path 330 can be checked based on the acquired information. As a result, when sample processing is performed by using the cartridge 300 capable of housing a sample and a reagent, whether the processing is appropriately performed in the cartridge 300 can be checked.

(Specific Exemplary Configuration of Measurement Device)

The following describes a specific exemplary configuration of the measurement device 100 using the cartridge 300 with reference to FIGS. 3 to 7. In an example illustrated in FIGS. 3 to 7, the measurement device 100 is an immunoassay device that detects a detection material in a sample by utilizing antigen-antibody reaction and measures the detection material based on a result of the detection. The measurement device 100 performs measurement by using the cartridge 300 (refer to FIG. 8) as a disk-shaped cartridge.

The housing 40 includes a housing body 101 and a lid 102. The lid 102 is provided to cover the entire upper surface of the housing body 101. A disposition unit 103 on which the cartridge 300 is disposed is provided on the upper surface of the housing body 101. The lid 102 is capable of rotating relative to the housing body 101 and opening and closing in each of a state illustrated in FIG. 3 in which the disposition unit 103 is opened and a state illustrated in FIG. 4 in which the disposition unit 103 is covered.

Figure 3:
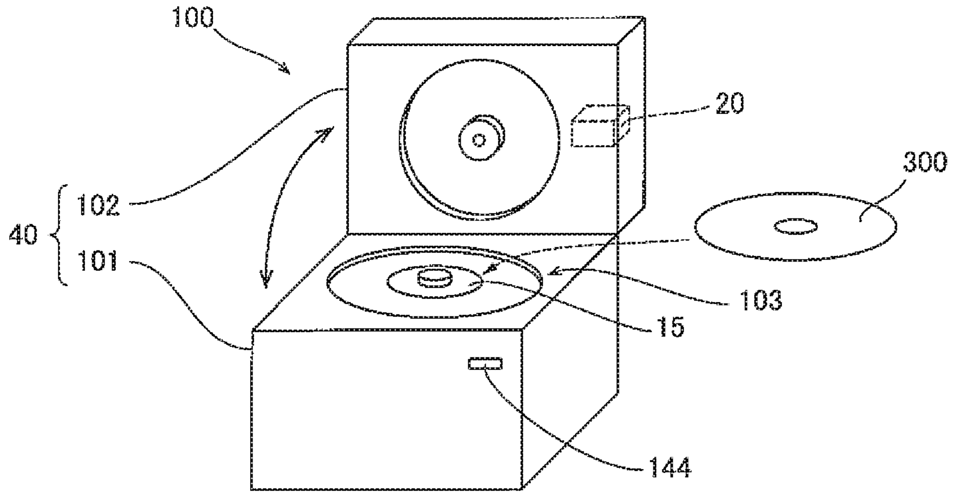
FIG. 3 is a perspective view illustrating a specific example of a measurement device when a lid is opened.
Figure 4:
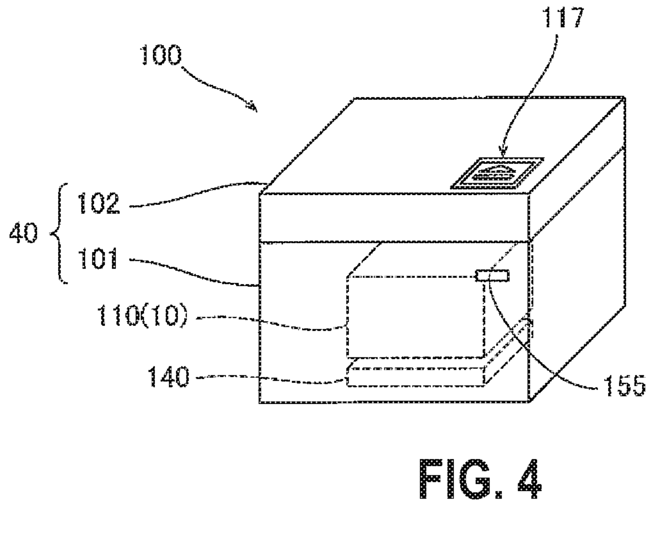
FIG. 4 is a perspective view illustrating a specific example of a measurement device when a lid is closed.

The measurement device 100 in FIGS. 3 and 4 is a display-less device including no display screen. Specifically, when used alone, the measurement device 100 does not perform operation input through a user interface.

<Internal Structure of Measurement Device>

Figure 5:
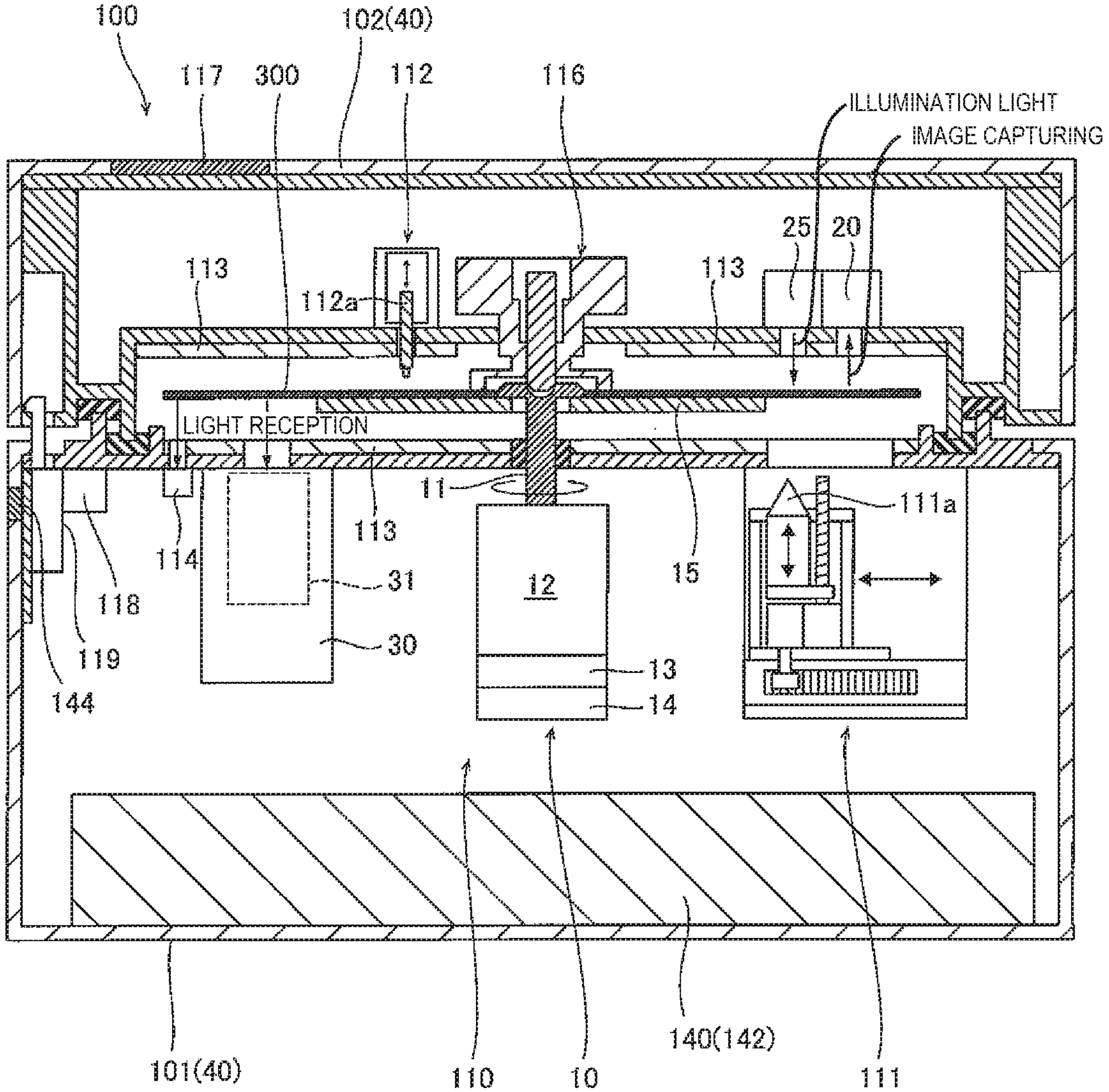
FIG. 5 is a pattern diagram illustrating a specific example of an internal structure of a measurement device.

The following describes the internal structure of the measurement device 100 with reference to FIG. 5. The measurement device 100 includes a measurement mechanism 110 used to measure a sample by using the cartridge 300.

The disposition unit 103 (refer to FIG. 3) serves as the upper surface of the housing body 101 covered by the lid 102 in an openable and closable manner. The disposition unit 103 is provided with a support member 15 that supports from below the cartridge 300. The support member 15 is, for example, a turntable. The support member 15 is provided at an upper end part of the rotational shaft 11 of the rotation mechanism 10.

In an example illustrated in FIG. 5, the measurement mechanism 110 includes the rotation mechanism 10, a magnet drive unit 111, a plugged opening unit 112, a heater 113, a temperature sensor 114, and the measurement unit 30.

The rotation mechanism 10 includes the rotational shaft 11 and the drive unit 12 as a motor. The rotation mechanism 10 drives the drive unit 12 to rotate, about the rotational shaft 11, the cartridge 300 installed on the support member 15. The rotation mechanism 10 includes an encoder 13 that detects the rotation angle of the drive unit 12, and an origin sensor 14 that detects the origin position of the rotation angle. The cartridge 300 can be moved to an optional rotational position by driving the drive unit 12 based on the detection angle of the encoder 13 with respect to the position detected by the origin sensor 14.

In the example illustrated in FIG. 5, the rotation mechanism 10 executes at least part of the measurement processing by rotating the cartridge 300 about the rotational shaft 11. As described later, the rotation mechanism 10 performs, as part of the measurement processing, processing such as centrifugation of a blood sample, transfer of the sample, transfer of a reagent to each of reaction chambers 314 to 319 (refer to FIG. 8), agitation of the reagent and the sample, and transfer of magnetic particles in the circumferential direction between the reaction chambers 314 to 319 inside the cartridge 300 through rotation.

The magnet drive unit 111 includes the magnet 111*a* and has a function to move magnetic particles inside the cartridge 300 in the radial direction. The magnet drive unit 111 is disposed below the disposition unit 103 and moves the magnet 111*a* in the radial direction. The magnet drive unit 111 moves the magnet 111*a* toward or away from the cartridge 300. Magnetic particles 70 in the cartridge 300 are collected when the magnet 111*a* is moved toward the cartridge 300, and the collection of the magnetic particles 70 is canceled when the magnet 111*a* is moved away from the cartridge 300.

The plugged opening unit 112 causes a pin member 112*a*, which is movable relative to the cartridge 300, to protrude from above the cartridge 300 disposed at the disposition unit 103 and contact with the cartridge 300, thereby opening a sealing body 350 (refer to FIG. 8) in the cartridge 300 by pressing. After the opening, the plugged opening unit 112 separates the pin member 112*a* from the cartridge 300 and moves the pin member 112*a* to a retracted position where the pin member 112*a* is not in contact with the cartridge 300.

The heater 113 is provided at each of a position directly below the cartridge 300 disposed at the disposition unit 103 and a position directly above the cartridge 300. The heater 113 heats a specimen housed in the chamber 310 to a predetermined reaction temperature to promote reaction between a sample and a reagent. The temperature sensor 114 detects the temperature of the cartridge 300 by infrared.

The measurement unit 30 includes a light receiving unit at a position facing to the cartridge 300 disposed at the disposition unit 103 through an opening formed in the housing body 101. With this configuration, the measurement unit 30 detects, through the light receiving unit, light emitted from the reaction chamber 319 (refer to FIG. 8). The measurement unit 30 includes a light detector 31 that detects or measures light attributable to the detection material moved to the measurement position. The light detector 31 is, for example, a photomultiplier tube, a photoelectric tube, or a light diode. The light detector 31 outputs a pulsed waveform in accordance with received photons. The measurement unit 30 includes a circuit that counts photons at a constant interval based on an output signal from the light detector 31 and outputs a count value. Accordingly, a measurement result can be easily acquired through optical measurement by rotating the cartridge 300 to move the detection material to the measurement position. The optical measurement can be performed in a non-contact manner by the relatively small-sized light detector 31, and thus it is possible to reduce increase in the size of a device configuration when an aspect is applied to the small-sized measurement device 100 for PoC testing using the cartridge 300. Thus, the optical measurement may be preferable.

The measurement device 100 also includes a clamper 116, the image capturing unit 20, and an illumination unit 25.

The clamper 116 rotatably supports a central part of the upper surface of the cartridge 300 installed on the support member 15 when the lid 102 is closed. The cartridge 300 is supported between the support member 15 and the clamper 116. The clamper 116 can vertically stroke in a predetermined range and is pressed toward the support member 15 side. The clamper 116 is provided with a stroke detection sensor (not illustrated) connected with a control unit 140 to be described later. It is possible to detect, based on a difference in the amount of stroke of the clamper 116, a state in which the cartridge 300 is not installed, a state in which the cartridge 300 is appropriately installed, and a state in which the cartridge 300 is inappropriately installed due to positioning error or the like.

The image capturing unit 20 is provided facing to the upper surface of the cartridge 300 installed on the support member 15, and captures the image 22 of the cartridge 300. The image capturing unit 20 captures the image 22 of the cartridge 300 of the monitoring target MT. The image capturing unit 20 includes, for example, a CCD image sensor or a CMOS image sensor. The image capturing unit 20 acquires, for example, a color image. The image capturing unit 20 captures the image 22 in, for example, the format of a still image. The illumination unit 25 is, for example, a light-emitting diode, and generates illumination light at image capturing.

In the exemplary configuration illustrated in FIG. 5, the image capturing unit 20 is fixed at least in the measurement processing. With this configuration, the image capturing range 21 does not move in the measurement processing, but the monitoring target MT is moved to the image capturing range 21 through rotation of the rotation mechanism 10. Accordingly, it is possible to avoid occurrence of image blur or the like attributable to movement of the image capturing unit 20 and thus acquire the high-quality image 22 suitable for checking the status of the monitoring target MT. When the image capturing unit 20 is fixed, the monitoring target MT can be easily moved to the image capturing range 21 through rotation of the cartridge 300. The image capturing unit 20 may be movable in a situation other than the measurement processing.

In the exemplary configuration illustrated in FIG. 5, the image capturing unit 20 is fixed to the lid 102 covering the cartridge 300 and capable of opening and closing. With this configuration, since the image capturing unit 20 is fixed to the lid 102 unlike a configuration in which the image capturing unit is movable, the image 22 of the monitoring target MT can be acquired with a space-saving configuration sufficiently housed in a small-sized measurement device for PoC testing. The image capturing unit 20 directly faces to the upper surface of the cartridge 300 through a through-hole provided to the lid 102. In addition, the illumination unit 25 directly faces to the upper surface of the cartridge 300 through the through-hole provided to the lid 102.

The magnet 111*a* that collects magnetic particles is disposed at a position under the image capturing range 21. The image capturing unit 20 is disposed on a side opposite to the magnet 111*a* with respect to the cartridge 300. In the exemplary configuration illustrated in FIG. 5, the image capturing unit 20 provided to the lid 102 performs image capturing of the cartridge 300 on the support member 15 from above, and the magnet 111*a* provided to the housing body 101 is capable of collecting the magnetic particles 70 from below at a position under the image capturing range 21, while moving toward and away from the cartridge 300 on the support member 15. Since image capturing is performed from the side opposite to the magnet 111*a*, the magnet 111*a* is not photographed in the image 22 while the magnetic particles 70 are collected, and thus the image 22 including all collected magnetic particles 70 can be acquired. Accordingly, whether the magnetic particles 70 are appropriately collected can be easily checked based on the image 22.

The measurement device 100 illustrated in FIG. 5 also includes, for example, an operation unit 117 (refer to FIG. 4) that receives an operation by a user to open the lid 102, a sensing unit 118 that senses opening and closing of the lid 102, and a lock mechanism 119 that locks the lid 102 by engaging with the lid 102 being closed. The lid 102 is pressed by a pressing member (not illustrated) in a direction in which the lid 102 is opened. When lock of the lid 102 being closed is canceled, the lid 102 is opened by pressing force.

Figure 6:
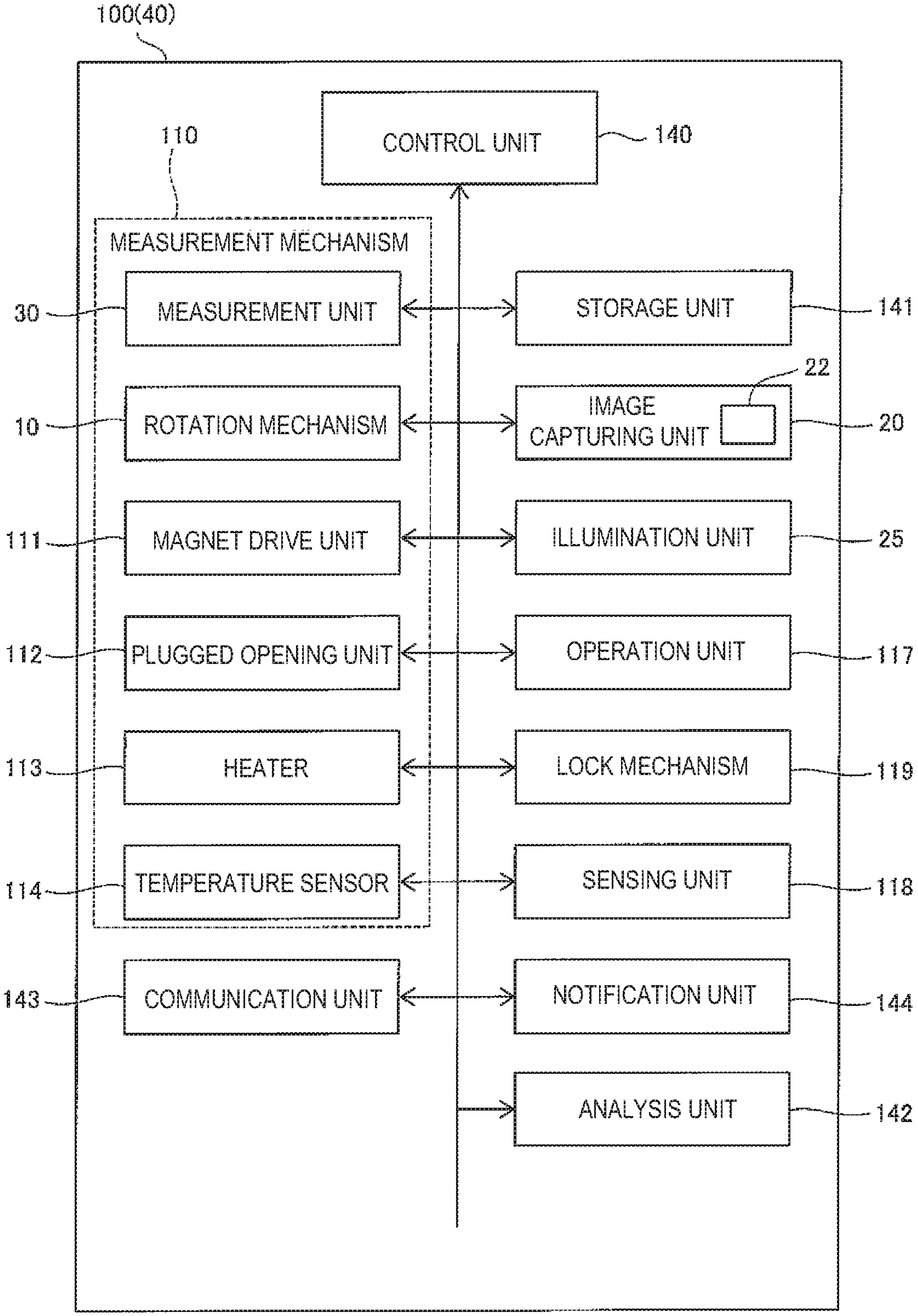
FIG. 6 is a block diagram illustrating an exemplary control configuration of a measurement device.

FIG. 6 illustrates a control configuration of the measurement device 100.

The measurement device 100 includes the control unit 140 or a controller. The control unit 140 includes, for example, a processor and a memory. The processor is, for example, a CPU or an MPU. The memory is, for example, a ROM or a RAM. The control unit 140 receives a signal from each component of the measurement device 100, and controls each component of the measurement device 100.

The measurement device 100 includes a storage unit 141. The storage unit 141 at least stores the captured image 22 of the monitoring target MT and measurement result data 50. The storage unit 141 is, for example, a flash memory or a hard disk.

The measurement device 100 includes an analysis unit 142 that analyzes the captured image 22. The analysis unit 142 analyzes the states of a sample and magnetic particles in the image 22 through image analysis on the image 22 of the monitoring target MT. Thus, whether the measurement processing is appropriately performed can be checked without determination based on the image 22 by a user. Since the measurement device 100 includes the analysis unit 142, the measurement device 100 can perform image analysis, which eliminates the need to perform communication with an external analysis device or the like to perform image analysis. As a result, the user does not need to prepare communication environment for image analysis, which improves device convenience. The analysis unit 142 includes, for example, a processor and a memory. The processor is, for example, a CPU or an MPU. The memory is, for example, a ROM or a RAM. The control unit 140 and the analysis unit 142 may be achieved by a common processor and a common memory, or may be each achieved by a separate processor and a separate memory.

Figure 7:
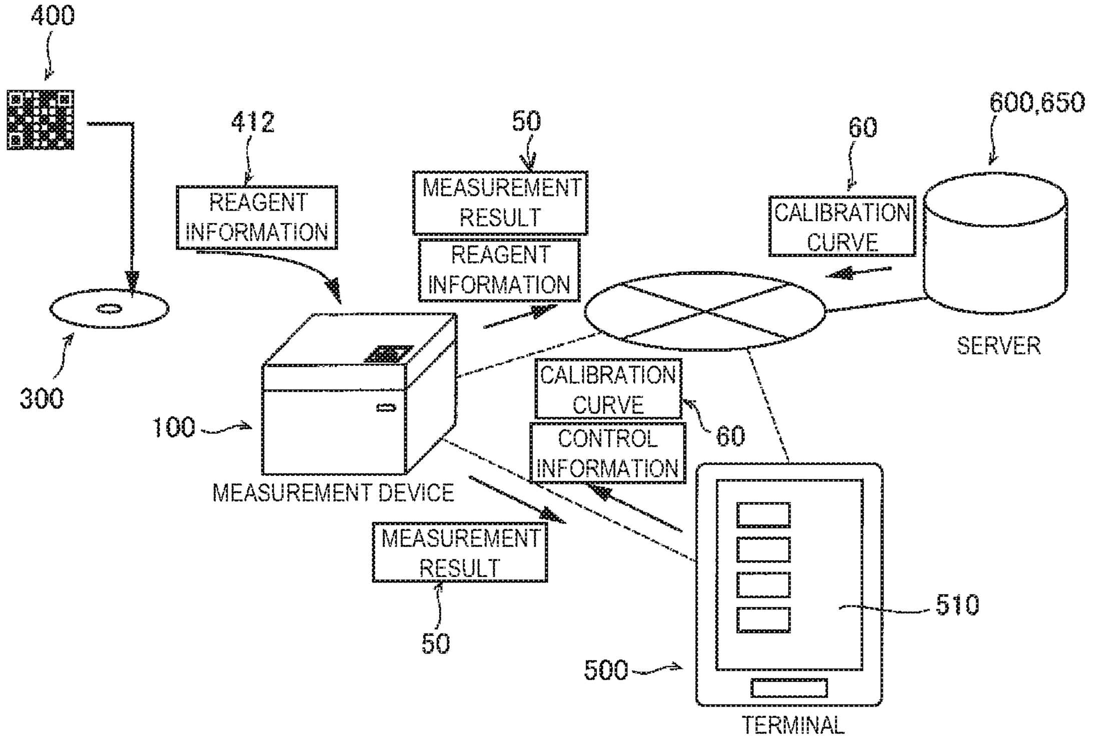
FIG. 7 is a diagram illustrating a network related to a measurement device.

The measurement device 100 includes a communication unit 143. The communication unit 143 can transmit information to an external instrument and receive information from the external instrument. The communication unit 143 includes, for example, a communication module or an external connection interface. As illustrated in FIG. 7, the communication unit 143 can perform, in a wired or wireless manner, communication with a terminal 500 capable of performing communication with the measurement device 100, and communication with servers 600 and 650 through a network. The communication unit 143 may be able to perform communication in kinds of communication schemes. Connection with the network is achieved by, for example, a wired LAN or a wireless LAN. Connection with the terminal 500 may be achieved by a wired LAN, a wireless LAN, Bluetooth (registered trademark), or any other near field communication (NFC). Connection with the terminal 500 may be achieved by an external connection interface such as a USB. The server 600 manages the measurement result data 50, and the server 650 manages reagent information including a calibration curve.

The control unit 140 transmits information 412, such as a lot number, related to the reagent housed in the cartridge 300 to the terminal 500 or the server 650 through the communication unit 143, specifies a calibration curve 60 of measurement using the reagent specified by the information 412, and requests data transmission of the calibration curve 60. The control unit 140 acquires the specified calibration curve 60 as a response from the terminal 500 or the server 650 through the communication unit 143. The information 412 related to the reagent housed in the cartridge 300 can be read from an identifier 400 to be described later.

The control unit 140 transmits the measurement result data 50 obtained by using the cartridge 300 to at least one of the terminal 500 and the server 600 through the communication unit 143. When the measurement result data 50 is transmitted to the server 600, a user can browse measurement results by accessing to the server 600 through an optional device connectable to a network.

The terminal 500 includes portable information terminals such as a tablet terminal and a smartphone, and an information terminal such as a personal computer (PC). The terminal 500 receives an operation input by the user through a user interface such as a button displayed on a display screen 510. The input operation is sensed by a touch panel when a portable information terminal such as a tablet terminal or a smartphone is used, or sensed through a mouse, a keyboard, or any other input instrument when a terminal such as a PC is used.

The terminal 500 can browse a measurement result generated at the measurement device 100 through communication with the measurement device 100. The terminal 500 may transmit a predetermined operation command to the measurement device 100 through communication with the measurement device 100.

As illustrated in FIG. 6, the measurement device 100 includes a notification unit 144 (refer to FIG. 3) capable of notifying the state of the device by a method different from screen display. The notification unit 144 notifies the state of the device through at least one of light coloring, light emission, light flashing, sound, and information transmission to the terminal 500. Thus, the notification unit 144 may be an indicator that performs notification by light emission, or a speaker or buzzer that performs notification by sound. The notification unit 144 may be a communication module or external connection interface having a configuration identical to that of the communication unit 143. When the notification unit 144 is provided, notification can be performed in a manner easily recognizable by the user without using the display screen.

(Specific Exemplary Configuration of Cartridge)

The following describes a specific exemplary configuration of the cartridge 300. In the example illustrated in FIG. 8, the cartridge 300 is a disk-shaped cartridge made of a substrate 301 having a plate disk shape. Each component in the cartridge 300 is formed by bonding, to a through-hole part formed in the substrate 301, films (not illustrated) entirely covering both surfaces of the substrate 301 including the through-hole part. Each film bonded to the substrate 301 is made of a translucent member. The substrate 301 has a thickness that facilitates temperature adjustment of the cartridge 300 by the heater 113 to be described later. For example, the thickness of the substrate 301 is several millimeters, and specifically 1.2 mm approximately.

The substrate 301 is provided with a through-hole 302, and a sample processing region 303 including chambers 310, paths 330, six housing units 341, one housing unit 342, and an injection port 343. A sample is injected through the injection port 343. The sample is a blood sample of whole blood collected from a subject.

The through-hole 302 penetrates through the substrate 301 at the center of the substrate 301. The cartridge 300 is installed on the measurement device 100 so that the center of the through-hole 302 coincides with the center of the rotational shaft 11. Hereinafter, the radial and circumferential directions of a circle centered at the through-hole 302 are simply referred to as "the radial direction" and "the circumferential direction", respectively.

Figure 8:
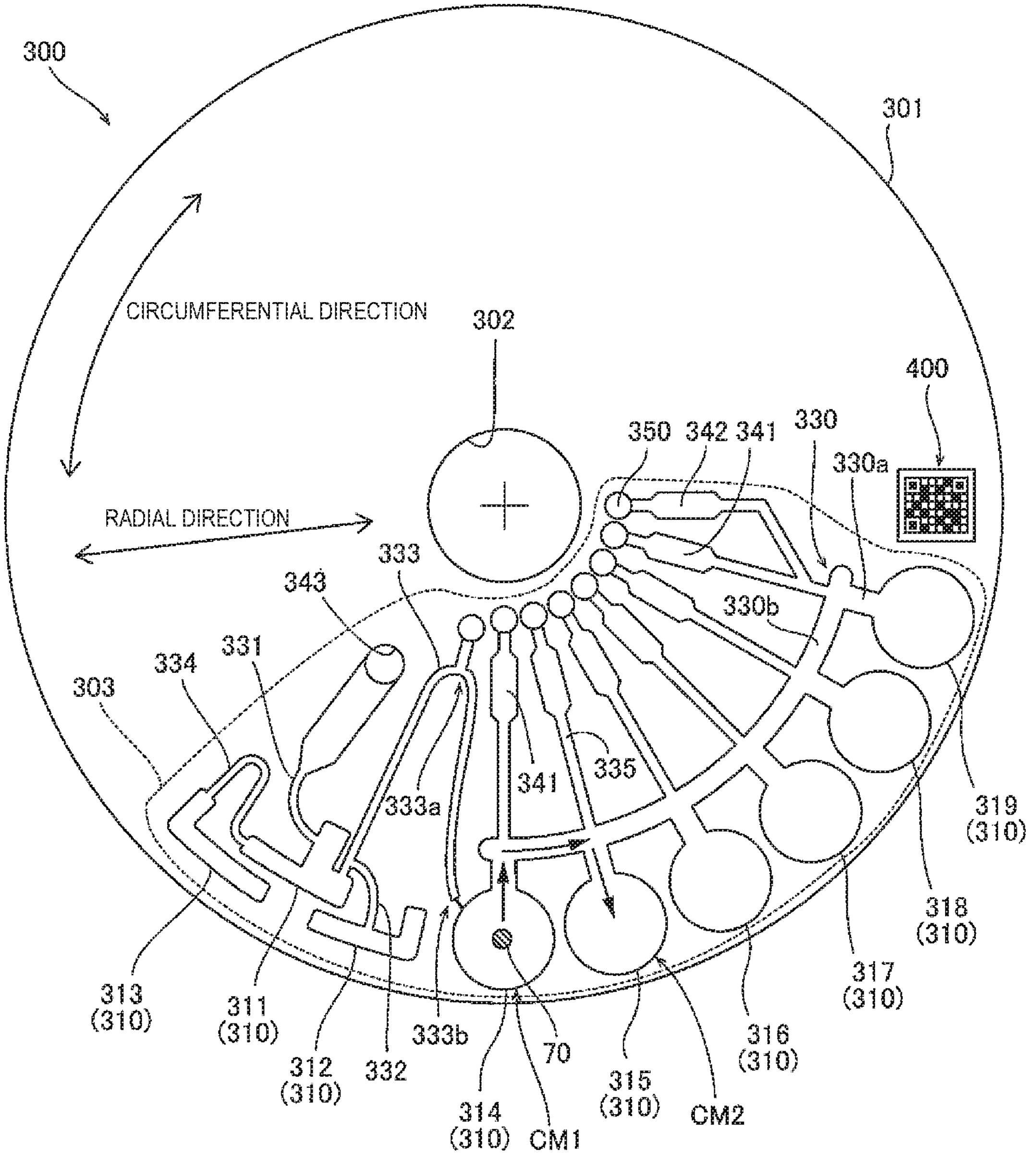
FIG. 8 is a diagram illustrating a specific example of a cartridge.

Each chamber 310 is a space capable of housing liquid. The chambers 310 are arranged in the circumferential direction near the outer periphery of the substrate 301. FIG. 8 illustrates an example in which the cartridge 300 is provided with nine chambers 310. As described later, the chambers 310 include a first chamber CM1 and a second chamber CM2.

The chambers 310 include a third chamber 311 in which the supplied sample is housed. The third chamber 311 is connected with the injection port 343 through a path 331. The blood sample injected through the injection port 343 is transferred to the third chamber 311 through the path 331 by centrifugal force generated by rotation of the cartridge 300.

The chambers 310 also include a fourth chamber 312 in which an excessive amount of the sample left after a certain amount of the sample is housed in the third chamber 311 is housed. The fourth chamber 312 is disposed outside of the third chamber 311 in the radial direction, and connected with the third chamber 311 through a path 332. The sample flowing from the path 331 into the third chamber 311 accumulates sequentially from outside in the radial direction by the centrifugal force, and the water surface position in the radial direction moves inward along with increase of the amount of accumulated fluid. When the water surface position in the third chamber 311 reaches the path 332, the sample in an exceeding amount is moved to the fourth chamber 312 by the centrifugal force. Thus, the sample in a certain amount can be accumulated in the third chamber 311 by injecting, in advance, the sample in an amount exceeding a certain amount.

The measurement processing includes processing of separating liquid and solid components included in the sample in the third chamber 311 by rotating the cartridge 300. Specifically, the sample in the third chamber 311 is separated, by centrifugation, into plasma as a liquid component and any other non-liquid component such as a blood cell as a solid component. The plasma separated in the third chamber 311 moves to a path 333 due to a capillary tube phenomenon. The path 333 is narrowed at a connection part 333*b* right before the reaction chamber 314 so that the plasma fills the path 333 to a position right before the reaction chamber 314.

The path 333 extends inward in the radial direction from the third chamber 311, bends at a bending part 333*a*, and extends outward in the radial direction, thereby connecting with the reaction chamber 314. When centrifugal force is applied by rotation while the path 333 is filled with the plasma, the plasma in a region on the reaction chamber 314 side of the bending part 333*a* is transferred to the reaction chamber 314. The volume of the path 333 between the bending part 333*a* and the leading end measures the plasma in a predetermined amount to be transferred to the reaction chamber 314.

The chambers 310 also include a fifth chamber 313 that prevents the sample in the third chamber 311 transferred to the reaction chamber 314 from being transferred to the reaction chamber 314 again. The fifth chamber 313 is disposed outside of the third chamber 311 in the radial direction and connected with the third chamber 311 through a path 334. When the plasma is transferred to the reaction chamber 314 through the path 333, the path 334 is filled with the sample. In the path 334, the sample is transferred from the third chamber 311 to the fifth chamber 313 by the principle of siphon until the water surface position reaches a balancing position. As a result, the amount of fluid in the third chamber 311 decreases, which prevents the sample in the third chamber 311 from being transferred to the reaction chamber 314 once the plasma is transferred to the reaction chamber 314.

The chambers 310 include the first chamber CM1 in which the detection material and the reagent are mixed, and the second chamber CM2 to which the detection material is transferred from the first chamber CM1 through the path 330. In FIG. 8, the six reaction chambers 314, 315, 316, 317, 318, and 319 having substantially identical shapes are arrayed side by side adjacent to each other in the circumferential direction and connected with each other through the path 330 extending in the circumferential direction. As described later, the detection material is sequentially transferred one by one between the six reaction chambers 314 to 319 from one side (the reaction chamber 314 side) toward the other side (the reaction chamber 319 side) through the path 330.

The first chamber CM1 and the second chamber CM2 are concepts indicating, among two reaction chambers adjacent to each other, an upstream reaction chamber and a downstream reaction chamber on a path through which the detection material is transferred. Among the six reaction chambers 314 to 319, the reaction chamber 314 to which the detection material is transferred first is the first chamber CM1. The reaction chamber 319 to which the detection material is transferred last is the second chamber CM2. The four reaction chambers 315 to 318 in the middle each serve as the second chamber CM2 for a reaction chamber on the upstream side, and as the first chamber CM1 for a reaction chamber on the downstream side.

The reagent housed in each housing unit 341 is transferred to the corresponding one of the reaction chambers 314 to 319 through a flow path 335. Liquid containing the detection material is transferred to the reaction chamber 314 through the path 333. The liquid containing the detection material is plasma separated from a whole blood sample by centrifugation as described later. The magnetic particles 70 are encapsulated in the reaction chamber 314. In the reaction chamber 314, the detection material contained in the sample is a composite body with the magnetic particles 70. Thus, in each reaction chamber following the reaction chamber 314, the detection material connected with the magnetic particles 70 are transferred to the path 330 and another chamber 310 by combination of rotation of the cartridge 300 and magnetic force.

In this manner, when the detection material contained in the sample is a composite body with the magnetic particles 70, the detection material can be transferred between the chambers 310 through the path 330 by attracting the magnetic particles by magnetic force. As a result, the detection material can be transferred in an optional direction in the cartridge 300 by combination of attraction of the magnetic particles by magnetic force and rotation of the cartridge 300, which facilitates transfer of the detection material.

The path 330 includes six radial direction regions 330*a* extending in the radial direction, and an arc-shaped circumferential direction region 330*b* extending in the circumferential direction. The circumferential direction region 330*b* is connected with the six radial direction regions 330*a*. The six radial direction regions 330*a* are connected with the reaction chambers 314 to 319, respectively. The six housing units 341 are connected with the path 330 through flow paths in the radial direction. The six housing units 341 are disposed side by side with the corresponding reaction chambers 314 to 319 in the radial direction. The housing unit 342 is connected with, through the flow path 335 mainly extending in the radial direction, the flow path 335 connecting the reaction chamber 319 and the housing units 341. The seven housing units 341 and 342 are disposed on the inner periphery side of the cartridge 300, and the six reaction chambers 314 to 319 are disposed on the outer periphery side of the cartridge 300.

The housing units 341 and 342 each houses the reagent, and include a sealing body 350 on an upper surface on the inner side in the radial direction. The sealing body 350 can be opened when pressed by the plugged opening unit 112 of the measurement device 100 from above. The reagent in the housing units 341 does not flow to the path 330 before the sealing body 350 is opened, but the reagent in the housing units 341 flows to the path 330 when the sealing body 350 is opened. When the cartridge 300 is rotated, the reagent moves to the corresponding one of the reaction chambers 314 to 319 by centrifugal force.

The housing units 341 and 342 each house the reagent for one measurement. Thus, the cartridge 300 includes the housing units 341 and 342 each housing the reagent for one measurement on the detection material. The cartridges 300 thus configured house different reagents for one-time use, and thus quality control of the individual cartridges 300 cannot be collectively performed by measuring a control material. Thus, since it can be checked whether processing is appropriately performed in the cartridge 300 based on the image 22 of the monitoring target MT, the measurement device 100 according to one or more embodiments is useful particularly for quality control of measurement using the cartridge 300 including the housing units 341 each housing the reagent for one measurement.

The measurement processing includes processing of transferring a composite body of the detection material with the magnetic particles 70 from the first chamber CM1 to the second chamber CM2. Specifically, the magnetic particles 70 are moved by magnetic force in the radial direction between the inside of the reaction chamber 314 and the arc-shaped circumferential direction region 330*b* of the path 330. When the cartridge 300 is rotated, the magnetic particles 70 move in the arc-shaped circumferential direction region 330*b* in the circumferential direction. The magnetic particles 70 carrying or supporting the detection material are moved sequentially to the reaction chambers 314 to 319 by combination of the movement in the radial direction due to magnetic force and the movement in the circumferential direction due to rotation.

The measurement processing includes processing of agitating the detection material and the reagent in the first chamber CM1 through rotation of the cartridge 300. Specifically, the rotational speed of the cartridge 300 is changed to alternately repeat acceleration and deceleration. Liquid in the chamber 310 is moved forward and backward in the circumferential direction by the acceleration and deceleration so that the composite body is dispersed in the reagent.

In the measurement device 100, the magnetic particles 70 carry or support the detection material and a labeling material in the chamber 310 and are transferred sequentially to chambers, thereby agitating the reagent and the detection material in each of the reaction chambers 314 to 319. The magnetic particles carrying or supporting the detection material and the labeling material are finally moved to the reaction chamber 319, and measurement is performed through detection of the labeling material by the measurement device 100.

The sample processing region 303 in the example illustrated in FIG. 8 is formed only in a one-third region of the substrate 301. However, the present invention is not limited thereto, two additional sample processing regions 303 may be formed in the remaining two-third region of the substrate 301 so that the three sample processing regions 303 are provided to the substrate 301. One sample processing region 303 may be formed in a region larger than a one-third region of the substrate 301.

When the sample processing regions 303 are provided, each sample processing region 303 may be a sample processing region 303 for the same measurement item or may be sample processing regions 303 for different measurement items. When the sample processing regions 303 are provided for the same measurement item, measurement of the same measurement item can be performed a plurality of times with one cartridge 300. When the sample processing regions 303 are provided for different measurement items, measurement of a plurality of items can be performed on the same sample with one cartridge 300.

The numbers and shapes of the chambers 310 and the paths 330 are not limited to those illustrated in FIG. 8. The configuration of components of each sample processing region 303 is determined in accordance with the content of sample processing assay executed in the sample processing region 303.

<Identifier>

In the exemplary configuration illustrated in FIG. 8, the cartridge 300 is provided with the identifier 400. The identifier 400 is an information storage medium from which information can be read by image capturing. In FIG. 8, the identifier 400 is a two-dimensional code. The identifier 400 is provided to the cartridge 300 by bonding a label on which the two-dimensional code is printed or by directly printing the two-dimensional code on the surface of the cartridge 300. The identifier 400 may be a bar code.

Figure 10:
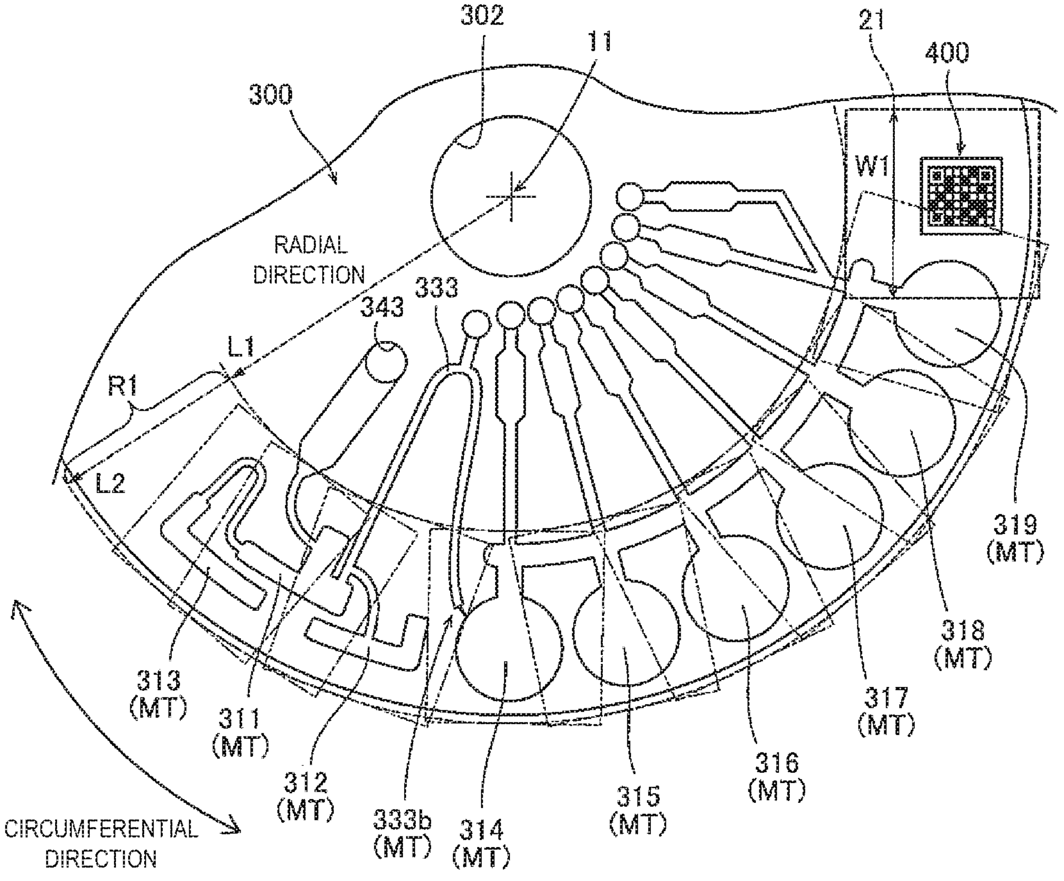
FIG. 10 is a diagram illustrating of a positional relation between each component of a cartridge and an image capturing range.

The rotation mechanism 10 rotates the cartridge 300 to move the identifier 400 that is provided to the cartridge 300 and from which information is read by image capturing to the image capturing range 21 (refer to FIG. 10). The image capturing unit 20 reads information recorded in the identifier 400 by capturing the image 22 of the identifier 400. In other words, the identifier 400 is read by the image capturing unit 20 that performs image capturing of the monitoring target MT. Accordingly, information used to perform the measurement processing can be read through image capturing of the monitoring target MT and image capturing of the identifier 400 only by rotating the cartridge 300. The control unit 140 controls the measurement operation based on the read information.

The identifier 400 includes at least one of information that specifies a measurement item measurable by using the cartridge 300, information on the reagent housed in the cartridge 300, and information that specifies the cartridge 300. Accordingly, when there are kinds of cartridges 300 of different measurement items, the information that specifies a measurement item can be used to specify a measurement item and perform processing in accordance with the measurement item. For example, when the expiration date of the reagent is acquired as the information 412 related to the reagent, whether the expiration date is passed can be checked. The information that specifies the cartridge 300 enables individual management of the cartridge 300 used in measurement. Thus, for example, the number of times of use may be counted to avoid wrong reuse of the cartridge 300 used a number of times exceeding an allowable number of times of use.

Figure 9:
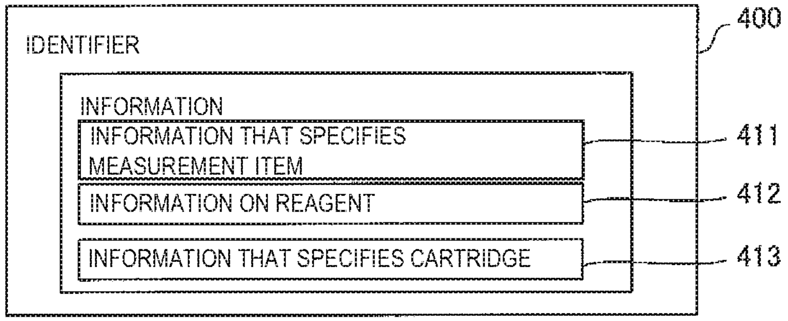
FIG. 9 is a diagram illustrating exemplary information recorded in an identifier.

In an example illustrated in FIG. 9, the identifier 400 includes information 411 that specifies a measurement item for the sample. For example, the information 411 that specifies a measurement item is a code indicating the measurement item, or the name of the measurement item. The control unit 140 controls the measurement unit 30 based on the information 411 that specifies a measurement item for the sample. Specifically, a measurement operation using the reagent in the cartridge 300 is determined based on the measurement item for the sample. As a result, in particular, when the measurement device 100 can measure kinds of measurement items by using kinds of cartridges 300, the measurement can be performed by an appropriate measurement operation in accordance with a measurement item.

Specifically, for example, the procedure of the measurement operation using the reagent, the duration of an individual operation, the content of the operation, and temperature setting are determined in accordance with a measurement item. For example, a measurement operation in accordance with a measurement item is preset in the measurement device 100. In other words, the information 411 that specifies a measurement item is information that specifies the kind of the cartridge 300.

In the example illustrated in FIG. 9, the identifier 400 includes the information 412 related to the reagent housed in the cartridge 300. The information 412 related to the reagent includes, for example, the lot number of the reagent. The information may include, for example, information that specifies the kind of the reagent, and the expire date of the reagent. The calibration curve 60 is acquired based on the information 412 related to the reagent.

In the example illustrated in FIG. 9, the identifier 400 includes information 413 that specifies the cartridge 300. The information 413 that specifies the cartridge 300 is a container ID that uniquely identifies the cartridge 300. The container ID may be any information unique to the individual cartridge 300, such as a manufacturing number or a dedicated identification number other than the manufacturing number. In this case, the control unit 140 associates a result of measurement by the measurement unit 30 with the information 413 that specifies the cartridge 300. Accordingly, the cartridge 300 used in the measurement can be identified, and thus the measurement result can be easily managed. For example, it is possible to avoid inappropriate measurement by specifying use of a container other than a legitimate product and reuse of a used container, thereby improving the reliability of the device.

All information recorded in the identifier 400 may be encrypted information. In this case, the information recorded in the identifier 400 is insignificant encrypted information. The information is read by the image capturing unit 20 and converted into the lot number of the reagent, a measurement item, the container ID of the cartridge 300, and the like through decoding by a predetermined decoding method at the control unit 140.

<Image Capturing of Monitoring Target>

As illustrated in FIG. 5, the image capturing unit 20 is provided at a position facing to the surface of the cartridge 300. Thus, as illustrated in FIG. 10, the image capturing range 21 is disposed on a circumferential movement path on which the monitoring target MT moves with rotation. With this configuration, the monitoring target MT can be reliably positioned in the image capturing range 21 within one rotation of the cartridge 300 without moving the image capturing range 21 relative to the cartridge 300. Then, the image 22 of the monitoring target MT can be acquired in a direction facing to the monitoring target MT, and thus the image 22 based on which the status of the monitoring target MT can be easily checked can be acquired. Each region illustrated with dashed and double-dotted lines in FIG. 10 is provided for convenience to indicate the relative positional relation the image capturing range 21 and each monitoring target MT when the monitoring target MT is moved to the image capturing range 21, and the region does not indicate that the image capturing range 21 moves.

The image capturing range 21 is set to be a range in which the distance from the rotational shaft 11 is between L1 and L2 inclusive (L2>L1) so that the image capturing range 21 includes the monitoring target MT provided in a range in which the distance from the rotational shaft 11 in the cartridge 300 is between L1 and L2 inclusive. With this configuration, it is possible to capture the image 22 in which the monitoring target MT is entirely included in the image capturing range 21 at least in the radial direction. Thus, it is possible to capture the image 22 based on which the status of the monitoring target MT can be more easily checked.

A width W1 of the image capturing range 21 in the circumferential direction is set to be equal to or larger than the width of each chamber 310 in the circumferential direction. In other words, the width W1 of the image capturing range 21 in the circumferential direction is equal to or larger than the width of the chamber 310 having a maximum width in the circumferential direction among the chambers 310.

In the exemplary configuration illustrated in FIG. 10, the image capturing range 21 is disposed on the movement paths of the monitoring targets MT disposed in an arc shape at which the distance from the rotational shaft 11 is substantially equal in the cartridge 300. Specifically, in FIG. 10, the nine chambers 310 are disposed in an arc shape at which the distance from the rotational shaft 11 is substantially equal. Thus, the movement paths of the nine chambers 310 along with rotation of the cartridge 300 are loci in circular rings having substantially equal rotational radii. The image capturing range 21 is set on these movement paths. The nine chambers 310 as the monitoring targets MT are positioned in the image capturing range 21 through rotation of the cartridge 300 and subjected to image capturing by the image capturing unit 20. Accordingly, the monitoring targets MT provided at different places can be moved into the image capturing range 21 only by rotating the cartridge 300, and subjected to image capturing. Thus, when there is a plurality of monitoring targets MT, the image 22 of each monitoring target MT can be easily acquired without providing a plurality of image capturing units 20 nor moving the image capturing unit 20.

In the example illustrated in FIG. 10, the nine chambers 310 are each disposed in a range R1 in which the distance from the rotational shaft 11 is between L1 and L2 inclusive. In addition, the path 330 is provided in the range R1 in which the distance from the rotational shaft 11 is between L1 and L2 inclusive. With this configuration, when image capturing is performed on each of the reaction chambers 314 to 319, the image capturing can be performed simultaneously on not only the chamber 310 but also the path 330 connected with the chamber 310. The range R1 in which the distance from the rotational shaft 11 is between L1 and L2 inclusive includes the connection part **333*b* of the path 333 connected with the reaction chamber 314. With this configuration, when image capturing is performed on the reaction chamber 314, the image capturing can be performed simultaneously on not only the reaction chamber 314 but also the connection part 333***b* at the leading end of the path 333 connected with the reaction chamber 314.

In this manner, in the exemplary configuration illustrated in FIG. 10, the nine chambers 310 can be moved to the image capturing range 21. The image capturing unit 20 can individually perform image capturing of each of the nine chambers 310. Each component of the path 330 can be moved together with the nine chambers 310 to the image capturing range 21. The image capturing unit 20 can perform image capturing of the path 330 connected with the reaction chambers 314 to 319 in a divided manner. The connection part 333*b* between the path 333 and the reaction chamber 314 can be moved to the image capturing range 21. The image capturing unit 20 can perform image capturing of the connection part 333*b* between the path 333 and the reaction chamber 314. Thus, the monitoring target MT can be each of the nine chambers 310, the path 330, and the connection part 333*b* between the path 333 and the reaction chamber 314. The monitoring target MT may be any one of, a plurality of, or all of these components.

In addition to the monitoring target MT, the above-described identifier 400 is included in the range R1 in which the distance from the rotational shaft 11 is between L1 and L2 inclusive. The identifier 400 is provided in advance at a predetermined position of the cartridge 300 in the circumferential direction in a predetermined positional relation relative to the sample processing region 303 in which the chambers 310 and the path 330 are provided. Specifically, the relative rotation angle of each monitoring target MT is set in advance with respect to a reading position of the identifier 400. The control unit 140 acquires a rotation angle to the reading position at which the identifier 400 is read with respect to an origin position detected by the origin sensor 14. The control unit 140 moves each monitoring target MT into the image capturing range 21 by controlling the rotation mechanism 10 based on the rotation angle at the reading position and the relative rotation angle of the monitoring target MT set in advance. Rotation control of the cartridge 300 in the measurement processing is performed based on the origin position, the reading position, and the relative rotation angle between each component of the cartridge 300 and the reading position. In this manner, the identifier 400 not only records information on measurement using the cartridge 300 but also functions as a rotational position reference in the cartridge 300.

When the cartridge 300 is set upside down to the measurement device 100, the identifier 400 cannot be read by the image capturing unit 20 through rotation of the rotation mechanism 10. Thus, the control unit 140 recognizes that the cartridge 300 is upside down when the identifier 400 cannot be read.

<Content of Image Analysis>

The following describes exemplary image analysis based on the image 22 of the monitoring target MT in the measurement processing.

Figure 11B:
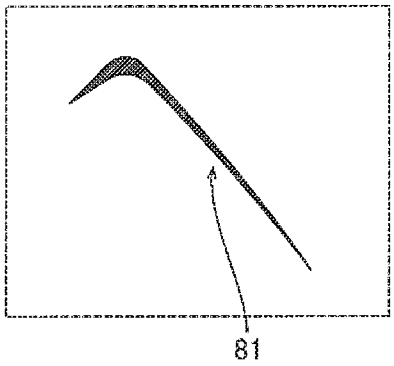
FIG. 11B is a diagram illustrating an analysis method.
Figure 11A:
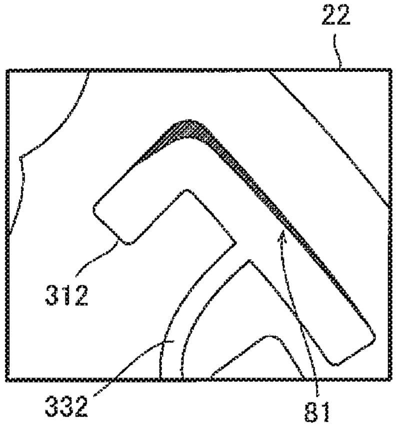
FIG. 11A is a diagram illustrating a fourth chamber.

In an example illustrated in FIG. 11A, the monitoring target MT includes the fourth chamber 312. The analysis unit 142 acquires information on the presence of the sample in the fourth chamber 312 based on the image 22 of the fourth chamber 312. As described above, when the sample in an amount exceeding a certain amount is transferred to the third chamber 311, the sample overflowing from the third chamber 311 flows into the fourth chamber 312. Thus, the analysis unit 142 acquires the information on the presence of the sample in the fourth chamber 312 by analyzing the presence of a region 81 having the color of the sample in the image 22 of the fourth chamber 312. For example, the analysis unit 142 detects the sample in the fourth chamber 312 through edge detection and parameter analysis of hue, saturation, luminance, and the like. For example, as illustrated in FIG. 11B, it is possible to determine whether the sample exists in the image 22 by extracting the region 81 of a pixel having hue, saturation, and luminance matching with those of the color of the sample acquired in advance in an allowable range. Accordingly, it can be checked that the sample in a certain amount is reliably housed in the third chamber 311 based on the presence of the sample in the fourth chamber 312. As a result, the measurement processing can be performed after checking that the sample in a sufficient amount necessary for achieving a certain accuracy of measurement is injected into the cartridge 300.

Figure 12B:
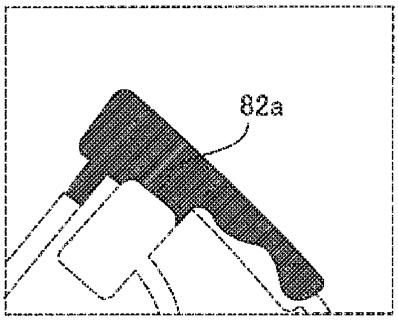
FIG. 12B is a diagram illustrating an analysis method.
Figure 12A:
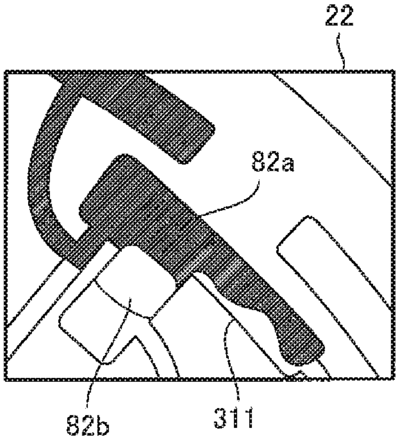
FIG. 12A is a diagram illustrating a third chamber.

In an example illustrated in FIG. 12A, the monitoring target MT includes the third chamber 311 in which the sample supplied to the cartridge 300 is housed. With this configuration, the measurement processing can be performed after it is checked whether the amount and property of the sample injected into the cartridge 300 are appropriate by capturing the image 22 of a state in which the sample collected from a subject is housed in the third chamber 311.

Specifically, when centrifugation is performed through rotation of the cartridge 300, a solid component such as a blood cell accumulates on the outer side in the third chamber 311 in the radial direction, and a liquid component such as a plasma accumulates on the inner side in the radial direction. In a blood sample, the solid component is red, and the liquid component is transparent. Thus, for example, as illustrated in FIG. 12B, the analysis unit 142 can detect the solid component in the image 22 of the third chamber 311 by extracting a region 82*a* having hue, saturation, and luminance matching with those of the color of the solid component acquired in advance in an allowable range in the image 22 through parameter analysis of hue, saturation, luminance, and the like. For example, the analysis unit 142 can also detect a region 82*b* of the liquid component through edge detection.

Accordingly, it is possible to determine the state of separation indicating whether the region 82*b* of the liquid component and the region 82*a* of the solid component are clearly separated from each other in the image of the third chamber 311. When the region 82*a* of the solid component has no clear boundary in the third chamber 311 and the region 82*a* of the solid component also exists on the inner side in in the third chamber 311 in the radial direction, this indicates a risk that centrifugation between the liquid component and the solid component is insufficient so that the liquid component and the solid component are not clearly separated, or that a pigment in a blood cell is mixed in the plasma due to hemolyzation.

For example, the analysis unit 142 acquires the volume of the solid component as an index of the amount of the solid component by multiplying the area of the detected region 82*a* of the solid component by the depth of the chamber 310, which is known. A hematocrit value, which is the ratio of a blood cell component included in the sample having a known volume, can be estimated based on the index of the amount of the solid component. In this manner, the analysis unit 142 acquires information on at least one of the state of separation and the amount of the solid component based on the area of the solid component in the image 22 of the third chamber 311. The analysis unit 142 preferably acquires both pieces of information, the state of separation and the amount of the solid component. Accordingly, the measurement processing can be performed after it is checked whether the separation processing is appropriately performed. In addition, the measurement processing can be performed after it is checked that the sample has no anomaly such as occurrence of hemolyzation in the sample or an abnormal hematocrit value.

Figure 13B:
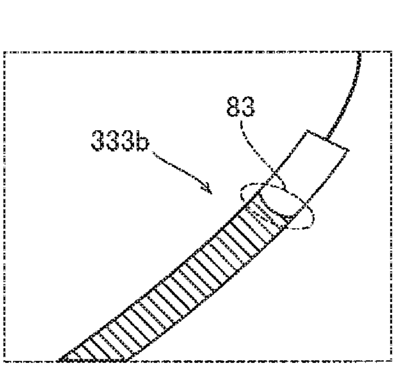
FIG. 13B is a diagram illustrating an analysis method.
Figure 13A:
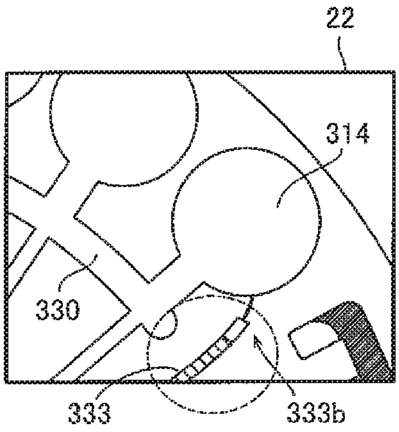
FIG. 13A is a diagram illustrating a connection part between a first chamber and a path.

In an example illustrated in FIG. 13A, the monitoring target MT includes the connection part 333*b* between the path 333 and the reaction chamber 314. As described above, the volume of the path 333 between the bending part 333*a* and the leading end measures the plasma in a predetermined amount to be transferred to the reaction chamber 314. Thus, the analysis unit 142 acquires information on the amount of the sample in the path 333 by analyzing the presence of an air bubble in the image 22 of the connection part 333*b* between the path 333 and the reaction chamber 314. For example, the analysis unit 142 performs edge detection of the connection part 333*b* in the image 22. When the path 333 is filled with the plasma, no water surface is formed inside the path 333, and thus the shape of the path 333 is detected. However, as illustrated in FIG. 13B, when the plasma does not reach a leading end part of the path 333 and there is an air bubble, a water surface 83 is formed inside the path 333. The analysis unit 142 detects the presence of an air bubble based on the presence of the water surface 83 inside the path 333 through edge detection. When an air bubble exists, the amount of the sample in the path 333 is smaller than a predetermined amount by the volume of the air bubble. Thus, the measurement processing can be performed after it is checked whether the predetermined amount of the sample is transferred to the path 333.

Figure 14B:
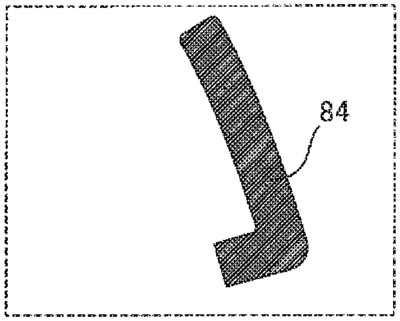
FIG. 14B is a diagram illustrating an analysis method.
Figure 14A:
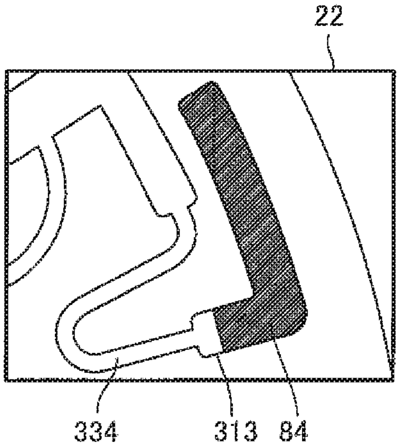
FIG. 14A is a diagram illustrating a fifth chamber.

In an example illustrated in FIG. 14A, the monitoring target MT includes the fifth chamber 313. As illustrated in FIG. 14B, the analysis unit 142 acquires information on the presence of the sample in the fifth chamber 313 by detecting a region 84 of the sample in the image 22 of the fifth chamber 313 and analyzing the presence of the region 84 of the sample. The information on the presence of the sample in the fifth chamber 313 can be acquired in a manner similar to the above-described acquisition of information of the fourth chamber 312. Accordingly, the following measurement processing can be performed after it is checked based on the presence of the sample in the fifth chamber 313 that there is no risk of part of the sample moving from the third chamber 311 to the chamber 310 in the measurement processing.

Figure 15B:
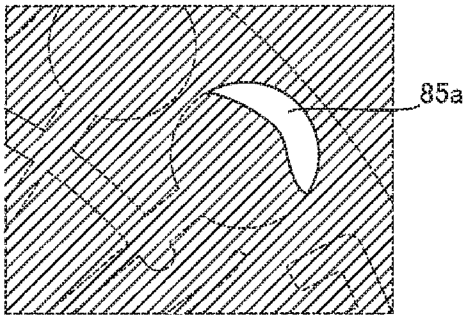
FIG. 15A is a diagram illustrating a first chamber to which a sample is transferred, and 15B is a diagram illustrating an analysis method.
Figure 15A:
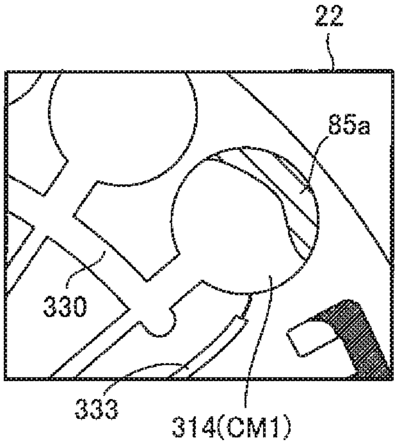

In an example illustrated in FIG. 15A, the monitoring target MT includes the first chamber CM1 in which the detection material and the reagent are mixed. The analysis unit 142 acquires information on at least one of the amount of the sample in the first chamber CM1 and the amount of the reagent in the first chamber CM1 based on the area of liquid in the image 22 of the first chamber CM1. Accordingly, the area of liquid when an appropriate amount of liquid is housed is acquired for a known volume of the first chamber CM1, and thus the amount of liquid in the first chamber CM1 can be checked based on the area of liquid in the image 22. As a result, the measurement processing can be performed after it is checked whether the sample and the reagent in appropriate amounts necessary for achieving a certain accuracy of measurement are correctly housed in the first chamber CM1.

Specifically, when the first chamber CM1 is, for example, the reaction chamber 314, plasma as the sample is transferred to the reaction chamber 314 through the path 333, and the reagent is transferred to the reaction chamber 314 from the housing unit 341. One or both of the amount of the sample and the amount of the reagent can be determined by transferring the sample and the reagent at different timings. For example, the analysis unit 142 detects, in the image 22 of the first chamber CM1, a region 85*a* (refer to FIG. 15B) of liquid in the space of the first chamber CM1 through edge detection and/or through parameter analysis of hue, saturation, luminance, and the like. When the sample is first transferred to the first chamber CM1, the volume of the sample is acquired as an index for the amount of the sample by multiplying the area of the region 85*a* of liquid in the image 22 before the reagent is transferred after the transfer of the sample by a known depth of the chamber 310. Whether the amount of the sample is appropriate can be determined based on whether the index for the amount of the sample is included in an allowable range.

Figure 16B:
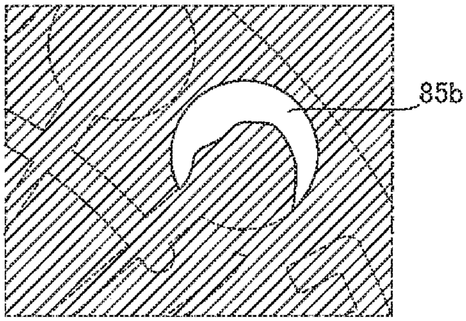
FIG. 16B is a diagram illustrating an analysis method.
Figure 16A:
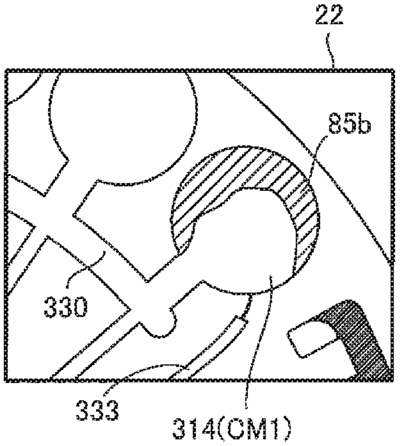
FIG. 16A is a diagram illustrating a first chamber to which a reagent is transferred.

Subsequently, as illustrated in FIG. 16A, the analysis unit 142 detects, in the image 22 after the transfer of the reagent, a region 85*b* of liquid in the space of the first chamber CM1 through edge detection and/or through parameter analysis of hue, saturation, luminance, and the like. A volume obtained by multiplying the area of the region 85*b* by the depth of the chamber 310 corresponds to the total amount of the sample and the reagent. Whether the total amount of the sample and the reagent is appropriate can be determined based on whether the total amount of the sample and the reagent is included in an allowable range. When the amount of the sample and the total amount are both appropriate, the amount of the transferred reagent is appropriate. The sample is not transferred to the reaction chambers 315 to 319, and thus whether the amount of the reagent is appropriate is determined by a method same as that for the case illustrated in FIGS. 15A and 15B.

Figure 17B:
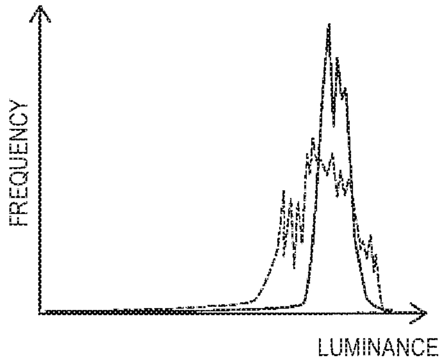
FIG. 17B is a diagram illustrating a dispersibility analysis method.
Figure 17A:
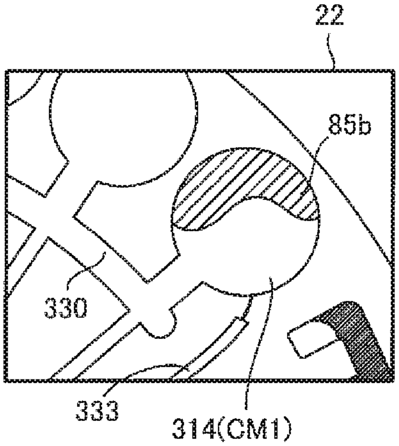
FIG. 17A is a diagram illustrating a first chamber after agitation processing.

In an example illustrated in FIG. 17A, the analysis unit 142 acquires information on uniformity of mixing of the detection material and the reagent based on grayscale of the image 22 of the first chamber CM1. Accordingly, as the detection material and the reagent are more sufficiently uniformly mixed, liquid parts in the image have more uniform colors. When the mixing is insufficient, grayscale variance occurs in the colors of the liquid parts. Thus, the uniformity of mixing of the detection material and the reagent can be checked based on grayscale variance between pixels in the image 22. As a result, the measurement processing can be performed while it is checked whether the detection material and the reagent are sufficiently uniformly mixed enough to achieve a certain accuracy of measurement.

Specifically, whether the mixing is uniformly performed can be determined based on whether the magnetic particles 70 are uniformly dispersed in the image 22 of the inside of the first chamber CM1 after agitation processing. The magnetic particles 70 are opaque particles having a predetermined color, and are relatively dark and dense at high concentration or relatively bright and faint at low concentration. Thus, the analysis unit 142 performs, for example, luminance histogram analysis based on color information of each pixel in the image 22 to obtain frequency distribution of the luminance value as illustrated in FIG. 17B. When the magnetic particles 70 are uniformly dispersed, each pixel has a substantially equal luminance value, and thus a high narrow peak (solid line part in FIG. 17B) is formed in the frequency distribution. When the mixing is ununiform and variance exists in the concentration of the magnetic particles 70, variance exists in the luminance value of each pixel due to the variance of the concentration, and thus a low wide peak (dashed line part in FIG. 17B) is formed in the frequency distribution. Accordingly, information on whether the detection material and the reagent are uniformly mixed can be acquired based on whether an evaluation index such as dispersion or half width of a peak is in an allowable range.

In an example illustrated in FIGS. 18 to 20, the monitoring target MT includes the first chamber CM1, and the second chamber CM2 to which a carrier carrying or supporting the detection material is transferred from the first chamber CM1 through the path 330. The analysis unit 142 acquires information on the amount of carriers transferred from the first chamber CM1 to the second chamber CM2 based on grayscale of the carrier in the image 22 of each of the first chamber CM1 and the second chamber CM2. In the example illustrated in FIGS. 18 to 20, the carriers are the magnetic particles 70. Accordingly, whether the amount of carriers has decreased through the transfer can be checked based on whether the color concentration of the carriers in an image of the second chamber CM2 after the transfer has decreased as compared to the color concentration of the carriers in an image of the first chamber CM1 before the transfer. As a result, the measurement processing can be performed by checking whether the transfer is appropriately performed without remaining of the detection material in the chambers 310 and the path 330 in the measurement processing.

Figure 18B:
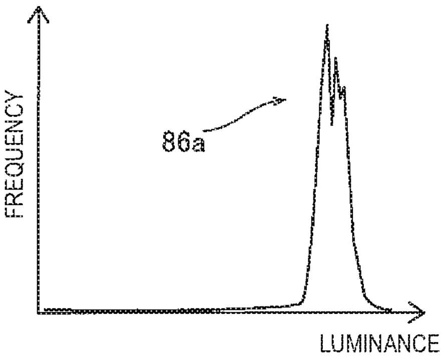
FIG. 18B is a diagram illustrating an analysis method.
Figure 18A:
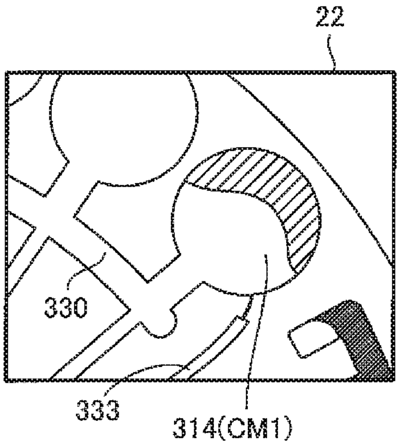
FIG. 18A is a diagram illustrating a first chamber after agitation processing.
Figure 19B:
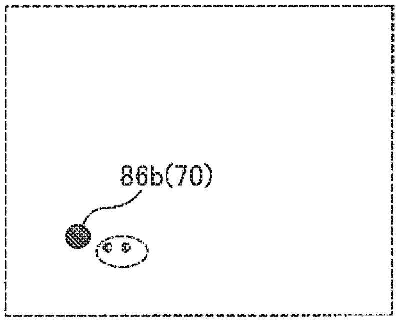
FIG. 19B is a diagram illustrating an analysis method.
Figure 19A:
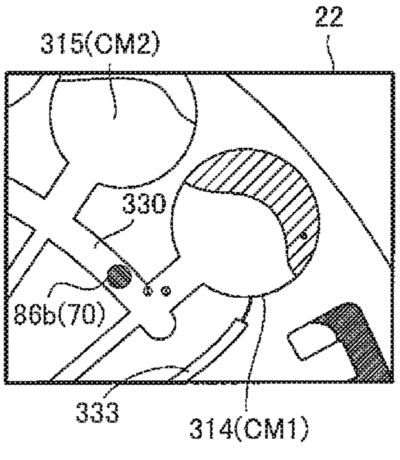
FIG. 19A is a diagram illustrating a path when magnetic particles are transferred.
Figure 20B:
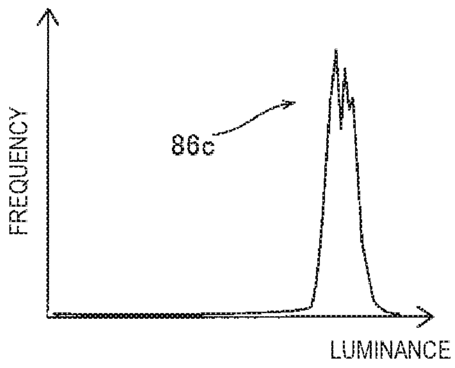
FIG. 20B is a diagram illustrating an analysis method.
Figure 20A:
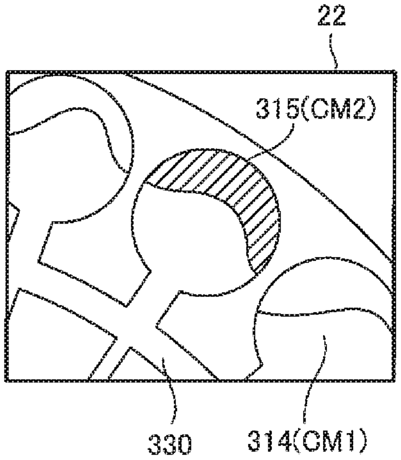
FIG. 20A is a diagram illustrating a second chamber after agitation processing.

Specifically, for example, as illustrated in FIG. 18A, the analysis unit 142 performs luminance histogram analysis based on color information of each pixel in the image 22 of the first chamber CM1 after agitation processing to obtain frequency distribution of the luminance value as illustrated in FIG. 18B. In the frequency distribution, a luminance value peak 86*a* reflecting the concentration of the magnetic particles 70 is formed in accordance with pixels in a liquid region in which the magnetic particles 70 are dispersed. Subsequently, as illustrated in FIG. 19A, agitation processing is performed after the magnetic particles 70 are transferred to the second chamber CM2 through the path 330 while being collected by the magnet 111*a*. As illustrated in FIG. 20A, the analysis unit 142 performs luminance histogram analysis in the image 22 of the second chamber CM2 after the agitation processing to obtain frequency distribution of the luminance value as illustrated in FIG. 20B. In the frequency distribution, a peak 86*c* of the luminance value reflecting the concentration of the magnetic particles 70 is formed for pixels in a liquid region in which the magnetic particles 70 are dispersed. When some magnetic particles 70 remain in collection or transfer, the amount of collected magnetic particles 70 changes through the transfer, and thus a peak shape changes between the frequency distribution of the image 22 of the first chamber CM1 and the frequency distribution of the image 22 of the second chamber CM2. The analysis unit 142 acquires the maximum value and/or average value of each peak as an index for the concentration of the magnetic particles 70. The analysis unit 142 acquires information on the amount of magnetic particles 70 transferred from the first chamber CM1 to the second chamber CM2 based on whether the concentration index is in an allowable range.

As illustrated in FIG. 19A, the image 22 can include the magnetic particles 70 being collected by the magnet 111*a* and transferred through the path 330. Thus, whether the transfer processing through the path 330 is normally performed can be determined by extracting a region 86*b* of the magnetic particles 70. Specifically, the monitoring target MT includes the first chamber CM1 and the path 330. As illustrated in FIG. 19A, the analysis unit 142 captures the image 22 when the transfer is being performed from the first chamber CM1 to the second chamber CM2 through the path 330. The analysis unit 142 acquires, for example, the longitudinal and transverse dimensions or area of the extracted region 86*b* as an index for the collection state of the magnetic particles 70. As illustrated with a dashed line in FIG. 19B, when the magnetic particles 70 remain, the longitudinal and transverse dimensions or area of the collected magnetic particles 70 changes, which allows determination of whether the magnetic particles 70 remain. In this manner, the analysis unit 142 acquires, based on whether the acquired index for the collection state is in an allowable range, information on whether the processing of transferring the magnetic particles 70 from the first chamber CM1 to the second chamber CM2 is normally performed.

In this manner, the rotation mechanism 10 rotates the cartridge 300 to move the monitoring targets MT into the identical image capturing range 21, and the image capturing unit 20 captures the image 22 including the monitoring targets MT.

Accordingly, the states of the monitoring targets MT can be collectively checked. Specifically, as illustrated in FIGS. 19A and 19B, for example, the status of transfer of the detection material from each chamber 310 to the path 330 can be easily checked by performing image capturing of the chamber 310 and the path 330.

The above-described method of analyzing the image 22 is merely exemplary. The image analysis may be performed by any method or based on any determination reference as long as it is possible to check whether processing executed on each monitoring target MT is normally performed.

(Description of Operation of Measurement Device)

Figure 21:
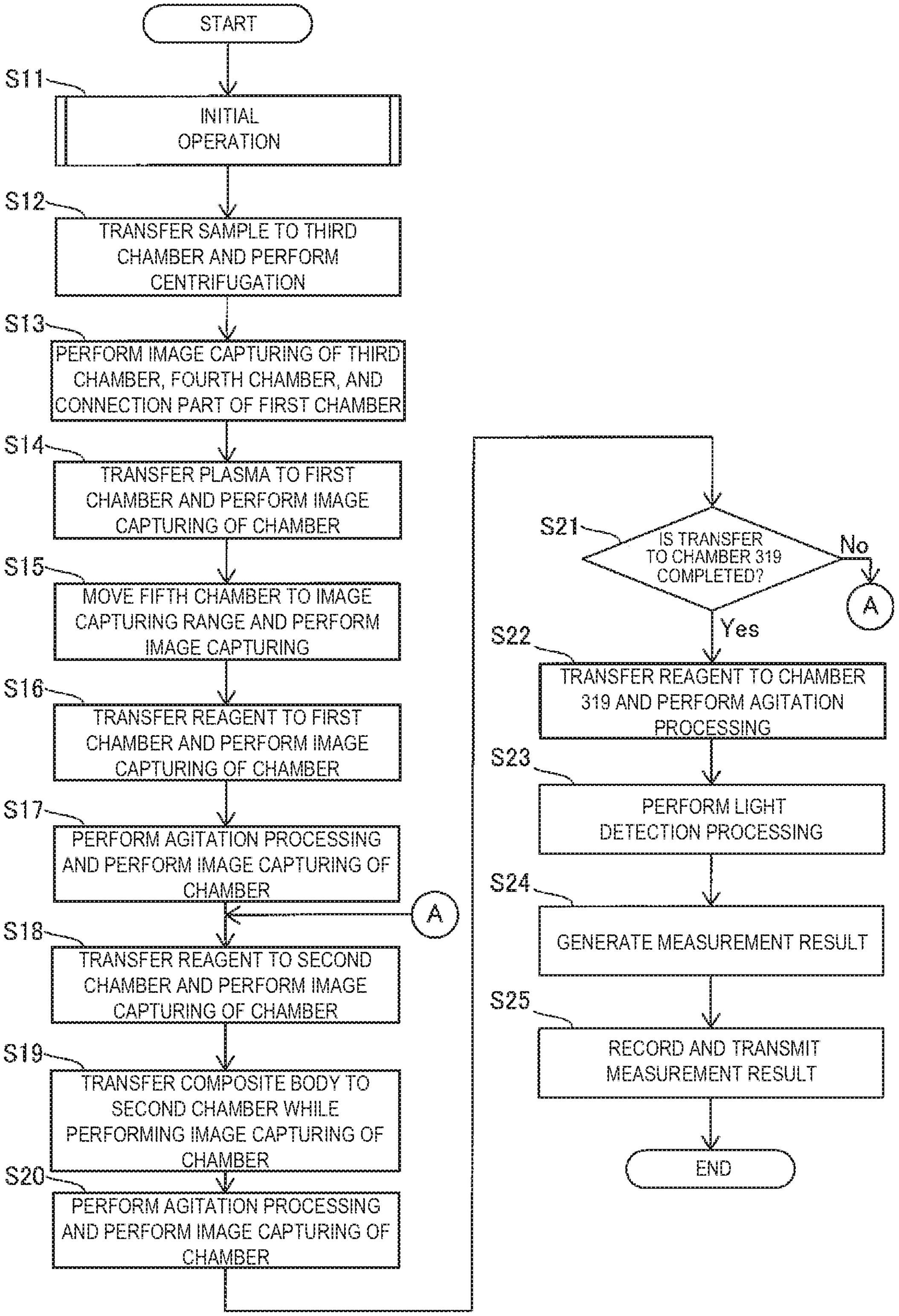
FIG. 21 is a flowchart illustrating a measurement operation of a measurement device.

The following describes operation of the measurement device 100 with reference to FIG. 21. In the following description, FIG. 5 should be referred to for the structure of the measurement device 100. FIG. 8 should be referred to for the structure of the cartridge 300.

First, in preparation work, a user injects, through the injection port 343 of the cartridge 300, a blood sample collected from a subject. The user injects, through the injection port 343, the sample in an amount larger than a predetermined amount that can be housed in the third chamber 311. Exemplary measurement of a hepatitis B surface antigen (HBsAg) is described as an exemplary measurement item of the cartridge 300. A detection material in the blood sample contains an antigen. The antigen is a hepatitis B surface antigen (HBsAg). The detection material may be one or a plurality of an antigen, an antibody, and a protein. The measurement item may be, for example, a prostatic specific antigen (PSA), thyroid stimulation hormone (TSH), or thyroid hormone (FT4).

A predetermined reagent is housed in the housing units 341 and 342 and the reaction chamber 314 of the cartridge 300 in advance. Specifically, R1 reagent is housed in the housing unit 341 positioned in the radial direction relative to the reaction chamber 314. R2 reagent is housed in the reaction chamber 314. R3 reagent is housed in the housing unit 341 positioned in the radial direction relative to the reaction chamber 315. Cleaning liquid is housed in the housing units 341 positioned in the radial direction relative to the reaction chambers 316 to 318. R4 reagent is housed in the housing unit 341 positioned in the radial direction relative to the reaction chamber 319. R5 reagent is housed in the housing unit 342.

At step S11 in FIG. 31, the control unit 140 executes an initial operation to start measurement.

Figure 22:
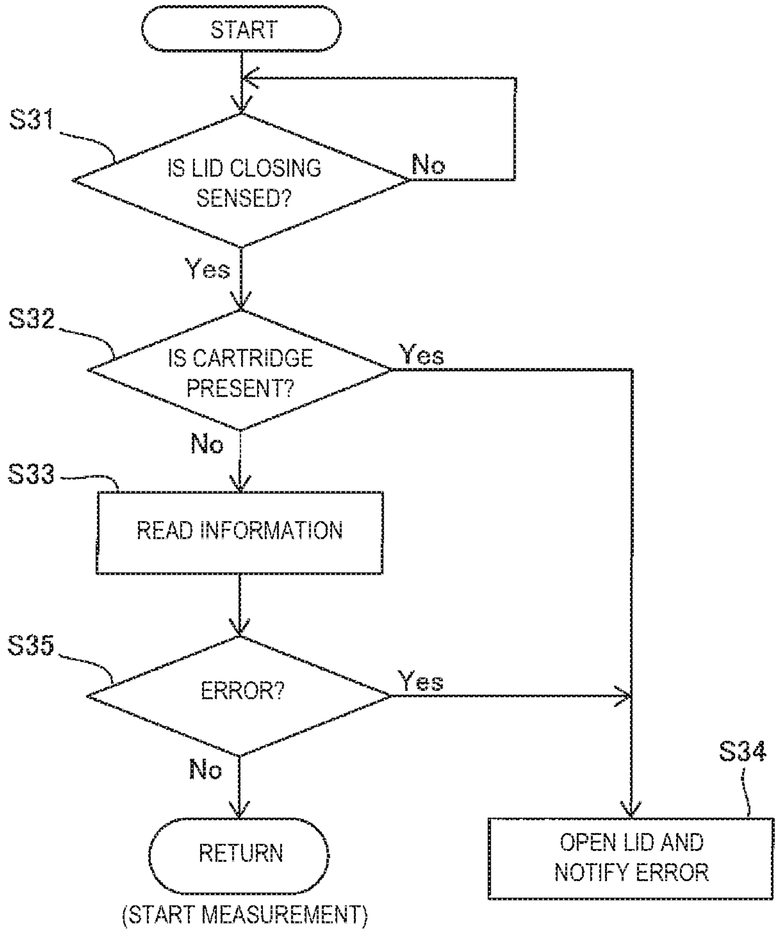
FIG. 22 is a flowchart illustrating an initial operation (subroutine) of a measurement device.

Specifically, at step S31 in FIG. 22, the control unit 140 determines whether the lid 102 is closed. The control unit 140 waits until the lid 102 is closed by the user. When the user opens the lid 102 and installs the cartridge 300 to the support member 15, and then closes the lid 102, the control unit 140 proceeds the process to step S32.

At step S32, the control unit 140 determines whether the cartridge 300 is in the device. The control unit 140 also determines whether the cartridge 300 is appropriately disposed in the device. Specifically, the control unit 140 checks whether the cartridge 300 exists and the cartridge 300 is disposed at an appropriate position based on the amount of stroke of the clamper 116. When the cartridge 300 does not exist or when the cartridge 300 is not normally installed, the control unit 140 proceeds to step S34.

When the cartridge 300 is appropriately disposed at the disposition unit 103, the control unit 140 executes an operation to read the identifier 400 at step S33. Specifically, the control unit 140 causes the rotation mechanism 10 to rotate the cartridge 300 so that the identifier 400 is disposed in the image capturing range 21 of the image capturing unit 20. The control unit 140 causes the illumination unit 25 to emit illumination light and the image capturing unit 20 to perform image capturing of a two-dimensional code as the identifier 400. The control unit 140 acquires, from the captured image, the information 411 that specifies a measurement item, the information 412 related to the reagent, and the information 413 that specifies the cartridge 300, which are recorded in the identifier 400. The control unit 140 also acquires the rotational position of each monitoring target MT based on an origin position detected by the origin sensor 14 and the reading position of the identifier 400.

At step S35, the control unit 140 determines whether there is error before measurement start. For example, when no information is read from the identifier 400 at step S33, the control unit 140 proceeds to step S34. At step S34, the control unit 140 notifies an error state through the notification unit 144 and opens the lid 102.

When it is determined at step S35 that there is no error before measurement start, the control unit 140 proceeds the process to step S12 in FIG. 21 and starts measurement by the measurement mechanism 110.

In FIG. 21, the control unit 140 starts the measurement operation by the measurement mechanism 110 at step S12 and the following steps. The control unit 140 selects a measurement operation pattern corresponding to the measurement item based on the information 411 that specifies the measurement item and is read by the image capturing unit 20, and controls operation of the measurement mechanism 110.

At step S12, the control unit 140 performs processing of transferring the sample to the third chamber 311 and processing of separating the sample into liquid and solid components. The control unit 140 rotates the cartridge 300 at fast speed through the rotation mechanism 10 and moves the sample from the path 331 to the third chamber 311 by centrifugal force. In this case, an excessive amount of the sample over a certain amount moves to the fourth chamber 312. In the third chamber 311, the sample is separated into the liquid component as plasma and the solid component such as a blood cell by the centrifugal force. The separated plasma moves into the path 333 and fills the path 333.

At step S13, the control unit 140 performs image capturing of each monitoring target MT after the centrifugation. The monitoring target MT includes the third chamber 311, the fourth chamber 312, and the connection part 333*b* between the path 333 and the first chamber CM1. The control unit 140 rotates the cartridge 300 through the rotation mechanism 10 to move the third chamber 311 as the monitoring target MT to the image capturing range 21, and captures the image 22 of the third chamber 311 through the image capturing unit 20. The analysis unit 142 analyzes the state of separation of the sample in the third chamber 311 and the amount of the solid component based on the image 22 (refer to FIGS. 12A and 12B).

The control unit 140 rotates the cartridge 300 through the rotation mechanism 10 to move the fourth chamber 312 as the monitoring target MT to the image capturing range 21, and captures the image 22 of the fourth chamber 312 through the image capturing unit 20. The analysis unit 142 analyzes the presence of the sample in the fourth chamber 312 based on the image 22 (refer to FIGS. 11A and 11B).

The control unit 140 rotates the cartridge 300 through the rotation mechanism 10 to move the connection part 333*b* as the monitoring target MT to the image capturing range 21, and captures the image 22 of the connection part 333*b* through the image capturing unit 20. The analysis unit 142 analyzes whether the path 333 is filled with the plasma up to the connection part 333*b* based on the image 22 (refer to FIGS. 13A and 13B).

At step S14, the control unit 140 performs processing of transferring the plasma in the path 333 to the first chamber CM1. The control unit 140 rotates the cartridge 300 through the rotation mechanism 10 to move the plasma from the path 333 to the first chamber CM1 by centrifugal force. In this case, the first chamber CM1 is the reaction chamber 314. Then, the control unit 140 rotates the cartridge 300 through the rotation mechanism 10 to move the first chamber CM1 as the monitoring target MT to the image capturing range 21, and captures the image 22 of the first chamber CM1 through the image capturing unit 20. The analysis unit 142 analyzes the amount of the sample in the first chamber CM1 based on the image 22 (refer to FIGS. 15A and 15B).

At step S15, the control unit 140 rotates the cartridge 300 through the rotation mechanism 10 to move the fifth chamber 313 as the monitoring target MT to the image capturing range 21, and captures the image 22 of the fifth chamber 313 through the image capturing unit 20. The analysis unit 142 analyzes the presence of the sample in the fifth chamber 313 based on the image 22 (refer to FIGS. 14A and 14B).

At step S16, the control unit 140 performs processing of transferring the reagent to the first chamber CM1. Specifically, the control unit 140 positions the cartridge 300 through the rotation mechanism 10, and drives the plugged opening unit 112 to open the sealing body 350 of the housing unit 341. The control unit 140 rotates the cartridge 300 through the rotation mechanism 10 to transfer the reagent housed in the housing unit 341 to the reaction chamber 314 by centrifugal force. Accordingly, the plasma, R1 reagent, and R2 reagent are mixed in the reaction chamber 314 as the first chamber CM1.

After the reagent transfer, the control unit 140 rotates the cartridge 300 through the rotation mechanism 10 to move the first chamber CM1 as the monitoring target MT to the image capturing range 21, and captures the image 22 of the first chamber CM1 through the image capturing unit 20. The analysis unit 142 analyzes the total amount of the sample and the reagent in the first chamber CM1 based on the image 22 (refer to FIGS. 16A and 16B).

At step S17, the control unit 140 performs processing of agitating liquid in the chamber 310. Specifically, the control unit 140 rotates the cartridge 300 through the rotation mechanism 10, repeating acceleration and deceleration during the rotation. Accordingly, the plasma, R1 reagent, and R2 reagent are mixed in the reaction chamber 314 as the first chamber CM1.

R1 reagent contains a capturing material to be connected with the detection material. The capturing material contains, for example, an antibody to be connected with the detection material. The antibody is, for example, a biotin-coupled HBs monoclonal antibody. R2 reagent contains a magnetic particle. The magnetic particle is, for example, a streptavidin coupled magnetic particle having a surface coated with avidin. At step S17, when the plasma, R1 reagent, and R2 reagent are mixed and the agitation processing is performed, the detection material and R1 reagent are connected with each other through antigen-antibody reaction. Then, the detection material connected with the capturing material of R1 reagent is connected with the magnetic particle through the capturing material by reaction between the antigen-antibody reaction body and the magnetic particle. As a result, a composite body in which the detection material and the magnetic particle are connected with each other is generated.

After the agitation processing, the control unit 140 rotates the cartridge 300 through the rotation mechanism 10 to move the first chamber CM1 as the monitoring target MT to the image capturing range 21, and captures the image 22 of the first chamber CM1 through the image capturing unit 20. The analysis unit 142 analyzes the uniformity of mixing of the sample and the reagent in the first chamber CM1 based on the image 22 (refer to FIGS. 17A and 17B).

Subsequently at step S18, the control unit 140 performs processing of transferring the reagent to the second chamber CM2. In this case, the second chamber CM2 is the reaction chamber 315. Specifically, the control unit 140 positions the cartridge 300 through the rotation mechanism 10, and drives the plugged opening unit 112 to open the sealing body 350 of the housing unit 341. The control unit 140 rotates the cartridge 300 through the rotation mechanism 10 to transfer the reagent housed in the housing unit 341 to the reaction chamber 315 by centrifugal force.

After the reagent transfer, the control unit 140 moves the second chamber CM2 as the monitoring target MT to the image capturing range 21, and captures the image 22 of the second chamber CM2 through the image capturing unit 20. The analysis unit 142 analyzes the amount of the reagent in the second chamber CM2 based on the image 22. This analysis processing is same as that described with reference to FIGS. 15 and 16.

Subsequently at step S19, the control unit 140 performs processing of transferring the composite body in the first chamber CM1 from the first chamber CM1 to the second chamber CM2. In this case, the first chamber CM1 is the reaction chamber 314, and the second chamber CM2 is the reaction chamber 315. The transfer processing is performed in the image capturing range 21 directly above the magnet 111*a*. Then, as illustrated in FIGS. 18 to 20, the control unit 140 acquires, through the image capturing unit 20, the images 22 of each of the first chamber CM1 and the second chamber CM2 before and after the transfer. The analysis unit 142 acquires information on the amount of the magnetic particles 70 transferred from the first chamber CM1 to the second chamber CM2.

When the composite body is transferred to the second chamber CM2, the control unit 140 performs agitation processing at step S20. The transferred composite body is dispersed in the reaction chamber 315. After the agitation, the control unit 140 performs image capturing of the second chamber CM2 through the image capturing unit 20. The analysis unit 142 analyzes the uniformity of mixing of the sample and the reagent in the second chamber CM2 based on the image 22.

At step S19, the composite body generated by the reaction chamber 314 is mixed with R3 reagent in the reaction chamber 315. R3 reagent contains a labeling material. The labeling material contains a capturing material to be differentially connected with the detection material, and a label. For example, the labeling material is a labeling antibody in which an antibody is used as the capturing material. A composite body in which the detection material, the capturing antibody, the magnetic particle, and the labeling antibody are connected with each other is generated by reaction between the composite body generated by the reaction chamber 314 and the labeling antibody contained in R3 reagent.

At step S21, the control unit 140 determines whether the composite body is completely transferred to the reaction chamber 319. When the composite body is not completely transferred to the reaction chamber 319, the control unit 140 returns the process to step S18, and repeats the processing at steps S18 to S20. Specifically, after the composite body is initially transferred from the reaction chamber 314 to the reaction chamber 315, the reagent transfer processing (step S18), the composite body transfer processing (step S19), and the agitation processing (step S20) are performed with the first chamber CM1 being set to be the reaction chamber 315 to which the composite body is transferred and the second chamber CM2 being set to be the reaction chamber 316 adjacent thereto on the downstream side. At each process, the control unit 140 performs image capturing of the corresponding chamber 310 and the path 330 through the image capturing unit 20. The analysis unit 142 analyzes each image 22.

When the composite body in the reaction chamber 315 is transferred from the reaction chamber 315 to the reaction chamber 316, the composite body generated in the reaction chamber 315 is mixed with the cleaning liquid in the reaction chamber 316. When agitation processing is performed, the composite body is separated from any unreacted material in the reaction chamber 316. In other words, the unreacted material is removed by cleaning in the reaction chamber 316.

When the composite body in the reaction chamber 316 is transferred from the reaction chamber 316 to the reaction chamber 317, the composite body generated in the reaction chamber 315 is mixed with the cleaning liquid in the reaction chamber 317. In the reaction chamber 317, too, any unreacted material is removed by cleaning.

When the composite body in the reaction chamber 317 is transferred from the reaction chamber 317 to the reaction chamber 318, the composite body generated in the reaction chamber 315 is mixed with the cleaning liquid in the reaction chamber 318. In the reaction chamber 318, too, any unreacted material is removed by cleaning.

When the composite body in the reaction chamber 318 is transferred from the reaction chamber 318 to the reaction chamber 319, the composite body generated in the reaction chamber 315 is mixed with R4 reagent in the reaction chamber 319. R4 reagent is a reagent for dispersing the composite body generated in the reaction chamber 315. R4 reagent is, for example, buffer solution.

When the composite body is transferred to the reaction chamber 319, the control unit 140 performs processing of transferring R5 reagent to the reaction chamber 319 at step S22. The control unit 140 positions the cartridge 300 through the rotation mechanism 10, and drives the plugged opening unit 112 to open the sealing body 350 of the housing unit 342. The control unit 140 rotates the cartridge 300 through the rotation mechanism 10 to transfer R5 reagent housed in the housing unit 342 to the reaction chamber 319 by centrifugal force. Accordingly, R5 reagent is further mixed in the reaction chamber 319.

R5 reagent is a luminescent reagent containing a luminescent substrate that emits light by reaction with the labeling antibody connected with the composite body. At step S22, when the mixed liquid generated in the processing up to step S20 is mixed with additionally transferred R5 reagent and subjected to agitation processing, a specimen is prepared. The specimen chemically emits light through reaction between the luminescent substrate and the labeling material connected with the composite body.

At step S23, the control unit 140 positions the reaction chamber 319 directly above the light receiving unit of the measurement unit 30 through the rotation mechanism 10, and detects, through the measurement unit 30, light emitted from the reaction chamber 319. At step S24, the control unit 140 performs measurement processing related to immunity based on the light detected by the measurement unit 30. The measurement unit 30 counts photons at a constant interval, and outputs a count value. The control unit 140 measures the presence, amount, and the like of the detection material based on the count value output from the measurement unit 30 and the acquired calibration curve 60, and generates a result of the measurement.

When the measurement result is obtained, at step S25, the control unit 140 records, as the measurement result data 50 in the storage unit 141, the measurement result in association with the information 413 that specifies the cartridge 300 and execution date and time of the measurement. The control unit 140 also transmits the measurement result data 50 to the server 600 through the communication unit 143.

Accordingly, the measurement operation of the measurement device 100 is completed.

As described above, the measurement processing includes the processes to be performed in a serial order illustrated in FIG. 21. In the process of measurement processing including the processes to be performed in a serial order, the image capturing unit 20 captures the image 22 of the monitoring target MT simultaneously or alternately with processing on the monitoring target MT. Specifically, the image capturing unit 20 performs image capturing simultaneously with transfer in the composite body transfer processing (step S19). In each of the centrifugation processing (step S12), the sample transfer processing (step S14), the reagent transfer processing (steps S16 and S18), and the agitation processing (steps S17 and S20), image capturing is performed until the next processing is performed after the processing, and thus the processing on the monitoring target MT and the image capturing of the monitoring target MT are alternately performed.

Accordingly, the series of processing can be sequentially executed while checking whether the processes to be performed in a serial order are each appropriately performed. Thus, when complicate measurement processing that involves processes is performed in the cartridge 300, the accuracy of the entire measurement processing can be maintained by checking the validity of each process.

In the above-described measurement operation, chemiluminescence is light emitted by using energy due to chemical reaction, and is, for example, light emitted when a molecule returns to the ground state after being excited into an excited state through chemical reaction. Chemiluminescence can be generated, for example, through reaction between an enzyme and a substrate, through application of an electrochemical stimulus to a labeling material, based on a luminescent oxygen channeling immunoassay (LOCI) method, or based on bioluminescence. In a first embodiment, any chemiluminescence may be employed. The detection material may be connected with a material that emits fluorescence when irradiated with light having a predetermined wavelength, thereby forming a composite body. In this case, a light source is disposed to irradiate the reaction chamber 319 with light. A light detector detects fluorescence emitted from a material connected with the composite body by light from the light source.

The magnetic particle may be a particle that contains a material having magnetism as a substrate and is used for normal immunoassay. For example, the magnetic particle may contain $Fe_2O_3$ and/or $Fe_3O_4$, cobalt, nickel, phyllite, or magnetite as a substrate. The magnetic particle may be coated with a connection material for connection with the detection material, or may be connected with the detection material through a capturing material for connection between the magnetic particle and the detection material. The capturing material is, for example, an antigen or antibody that mutually connects with the magnetic particle and the detection material.

The capturing material is not particularly limited, but may be any material that is differentially connected with the detection material. For example, the capturing material is connected with the detection material by antigen-antibody reaction. More specifically, the capturing material is an antibody, but when the detection material is an antibody, the capturing material may be an antigen of the antibody. When the detection material is a nucleic acid, the capturing material may be a nucleic acid complementary with the detection material. Examples of the label included in the labeling material include an enzyme, a fluorescent substance, and a radioactive isotope. Examples of the enzyme include, alkaline phosphatase (ALP), peroxidase, glucose oxidase, tyrosinase, and acid phosphatase. When the chemiluminescence is electrochemiluminescence, the label may be any material that emits light by an electrochemical stimulus, and is, for example, a ruthenium complex. Examples of the fluorescent substance include fluorescein isothiocyanate (FITC), green fluorescence protein (GFP), and luciferin. Examples of the radioactive isotope include 125I, 14C, and 32P.

When the label is an enzyme, a well-known luminescent substrate may be selected as a luminescent substrate for the enzyme as appropriate in accordance with the used enzyme. For example, when the enzyme is alkaline phosphatase, examples of the luminescent substrate include: chemiluminescence substrates such as CDP-Star (registered trademark), (4-chloroauric-3-(methoxyspiro [1,2-dioxetane-3,2'-(5'-chloroauric) tricyclo [3.3.1.13,7] decane]-4-yl) phenylphosphate 2 sodium), and CSPD (registered trademark) (3-(4-methoxyspiro [1,2-dioxetane-3,2-(5'-chloroauric) tricyclo [3.3.1.13,7] decane]-4-yl) phenylphosphate 2 sodium); luminescent substrates such as p-nitrophenylphosphate, 5-bromo-4-chloroauric-3-indolylphosphate (BCIP), 4-nitroblue tetra zolium chloride (NBT), and iodine nitro tetra zolium (INT); a fluorescence substrate such as 4-methylumbelliphenyl phosphate (4MUP); and coloring substrates such as 5-bromo-4-chloroauric-3-indolylphosphate (BCIP), 5-bromo-6-chloroauric-indolylphosphate 2 sodium, and p-nitrophenylphosphate.

Figure 23:
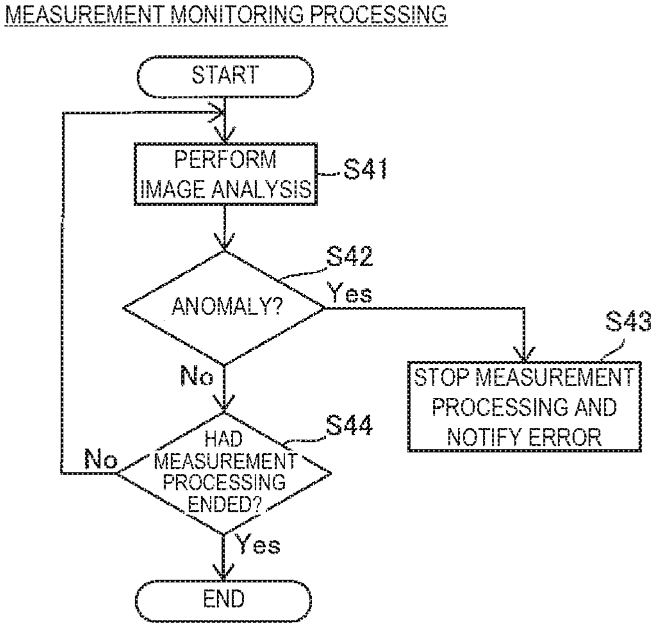
FIG. 23 is a flowchart illustrating exemplary measurement monitoring processing by image analysis.

The following describes measurement monitoring processing using a result of analysis of the image 22 by the analysis unit 142 with reference to FIG. 23. The measurement monitoring processing illustrated in FIG. 23 is executed at each acquisition of the image 22 during the measurement processing illustrated in FIG. 21.

In FIG. 23, the control unit 140 controls, based on information acquired by the analysis unit 142, outputting of a measurement result obtained by measuring the detection material. Accordingly, the user does not need to monitor the process of the measurement processing based on the image 22, but, for example, control can be performed to avoid outputting of the result of measurement by the measurement unit 30 when the acquired information indicates occurrence of anomaly in the measurement processing. In this case, outputting of the measurement result is avoided when a sufficient measurement accuracy cannot be achieved due to the occurred anomaly.

First at step S41, the analysis unit 142 performs image analysis on the acquired image 22. As illustrated in FIGS. 11 to 20, the content of the analysis differs in accordance with the monitoring target MT subjected to image capturing. The analysis unit 142 performs image analysis in accordance with the monitoring target MT and the content of previously performed processing.

At step S42, the control unit 140 determines whether the information acquired by the analysis unit 142 indicates anomaly as a result of the analysis. In other words, the control unit 140 determines whether the information acquired by the analysis unit 142 corresponds to any error item set in advance.

Specifically, when the sample does not exist in the image 22 of the fourth chamber 312 (refer to FIGS. 11A and 11B), a sample dispense amount is too small, and thus the analysis unit 142 outputs information on the corresponding error item. When the solid component exists on the inner side of a predetermined range in the radial direction in the image 22 of the third chamber 311 (refer to FIGS. 12A and 12B), centrifugation is insufficient or hemolyzation exists, and thus the analysis unit 142 outputs information on the corresponding error item. When the volume of the solid component is not in an allowable range in the image 22 of the third chamber 311 (refer to FIGS. 12A and 12B), the analysis unit 142 outputs information on the corresponding error item. When an air bubble exists in the fourth chamber 312 in the image 22 (refer to FIGS. 13A and 13B) of the connection part 333*b* between the path 333 and the reaction chamber 314, the amount of the sample in the path 333 is too small, and thus the analysis unit 142 outputs information on the corresponding error item. When the sample does not exist in the image 22 of the fifth chamber 313 (refer to FIGS. 14A and 14B), the sample potentially flows out to the first chamber CM1, and thus the analysis unit 142 outputs information on the corresponding error item.

When at least one of the amount of the sample and the amount of the reagent is smaller or larger than an allowable range in the image 22 of the first chamber CM1 (refer to FIGS. 15 and 16), the analysis unit 142 outputs information on the corresponding error item. When the uniformity of the magnetic particles is not in an allowable range in the image 22 of the first chamber CM1 (refer to FIGS. 17A and 17B), the uniformity of mixing of the detection material and the reagent is insufficiently achieved by agitation processing, and thus the analysis unit 142 outputs information on the corresponding error item. When a concentration index for the magnetic particles being collected is not in an allowable range in comparison (refer to FIGS. 18 and 20) between the image 22 of the first chamber CM1 and the image 22 of the second chamber CM2 when the composite body is transferred, the analysis unit 142 outputs information on an error item indicating that the transfer processing is not normally performed. When it is checked in the image 22 (refer to FIGS. 18 to 20) that the magnetic particles remain in the path 330, too, the analysis unit 142 outputs information on an error item indicating that the transfer processing is not normally performed.

When it is determined at step S42 that anomaly exists, the control unit 140 stops the measurement processing at step S43. The control unit 140 notifies the user of the error occurrence through the notification unit 144. Accordingly, at each step of the measurement processing illustrated in FIG. 21, when the image 22 is acquired and the information acquired by the analysis unit 142 indicates anomaly based on the acquired image 22, the measurement processing is stopped promptly. When the measurement processing is stopped due to anomaly, no measurement result is generated.

When it is determined at step S42 that no anomaly exists, the control unit 140 determines whether the measurement processing has ended at step S44. When the measurement processing has not ended, the process returns to step S41, and the analysis unit 142 performs image analysis on the subsequently acquired image 22. When the measurement processing has ended, the image analysis processing is ended.

As described above, in the example illustrated in FIG. 23, when the information acquired by the analysis unit 142 indicates anomaly, the control unit 140 performs control to stop measurement processing without outputting a measurement result. When the measurement processing has ended while no anomaly is detected in each image 22 acquired in the measurement processing, a measurement result is output. Accordingly, since the measurement processing is stopped when anomaly has occurred, it is possible to reliably avoid a measurement result at low reliability from being provided to the user.

(Modification of Image Analysis Processing)

In FIG. 23, when the information acquired by the analysis unit 142 indicates anomaly, control is performed to stop measurement processing without outputting a measurement result. However, in an example illustrated in FIG. 24, a measurement result is output also when the information acquired by the analysis unit 142 indicates anomaly.

Specifically, when image analysis is performed at step S41 and it is determined at step S42 that anomaly exists, the control unit 140 determines whether anomaly (in other words, an error item) indicated by the information acquired by the analysis unit 142 is set as a correction target at step S51.

Specifically, although various anomalies can occur in the measurement processing as described above, the measurement processing does not necessarily need to be stopped for, among the anomalies, an anomaly with which an appropriate measurement result can be calculated by correcting a measurement result. Thus, in the example illustrated in FIG. 24, a measurement result is corrected for an error item set in advance as an anomaly that can be handled through measurement result correction. When the occurred anomaly is set as a correction target at step S51, the control unit 140 sets a data correction flag at step S52. The data correction flag indicates that measurement result correction processing in accordance with the content of the anomaly is performed when a measurement result is generated.

When the occurred anomaly is not set as a correction target at step S51, an anomaly display flag is set at step S53. The anomaly display flag indicates that a measurement result is generated with information indicating the occurrence of anomaly in the measurement processing. In this case, the user can obtain a measurement result, knowing the occurrence of anomaly in the measurement processing.

At step S44, the control unit 140 determines whether the measurement processing has ended. When the measurement processing has not ended, the process returns to step S41. When the measurement processing has ended, the control unit 140 performs flag processing at step S54. Specifically, when the data correction flag is set in the measurement processing, the control unit 140 performs the measurement result correction processing in accordance with the occurred anomaly. When the anomaly display flag is set in the measurement processing, the control unit 140 performs processing of including, in a measurement result, information indicating the occurrence of anomaly in the measurement processing. When a flag is not set, processing corresponding to the flag is not performed. Then, at step S55, the control unit 140 generates data of the measurement result.

Figure 24:
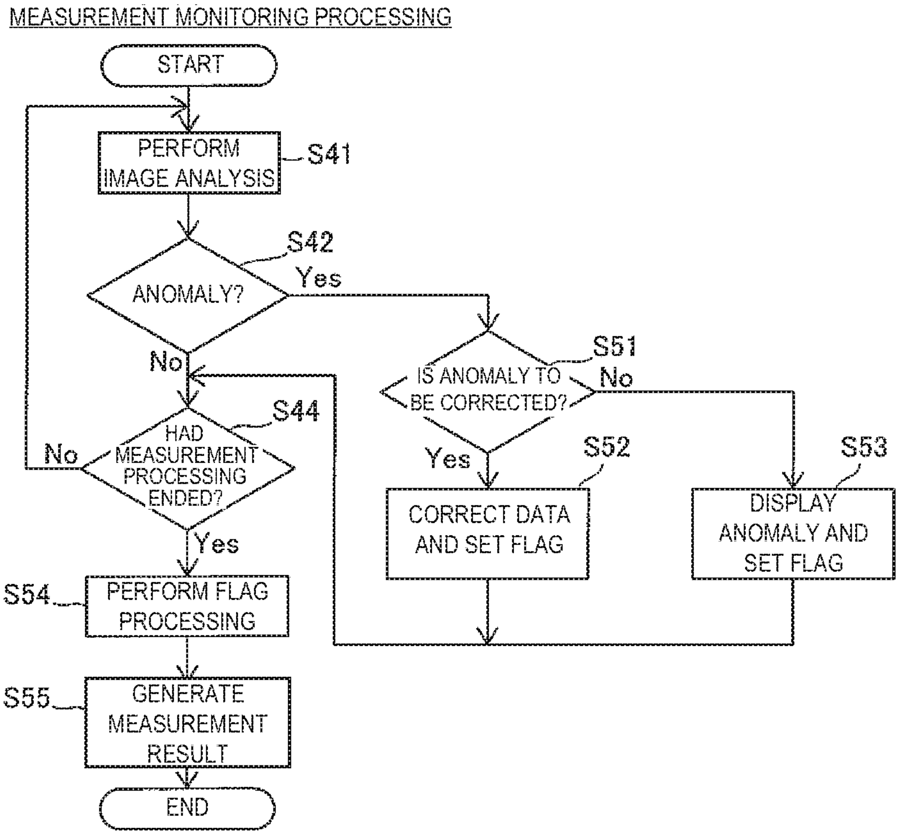
FIG. 24 is a flowchart illustrating measurement monitoring processing according to a modification.

In the example illustrated in FIG. 24, when the information acquired by the analysis unit 142 indicates anomaly, the control unit 140 performs control to stop the measurement processing without outputting a measurement result or output a measurement result with additional information indicating the occurrence of anomaly. Accordingly, when the acquired information indicates anomaly, a measurement result is output with additional information indicating the occurrence of anomaly, and thus the measurement result can be provided to the user while the user knows that the measurement result has low reliability. In a case of anomaly with which a sufficient accuracy can be obtained for a measurement result by correction, the measurement result is corrected and output when the anomaly has occurred so that an appropriate measurement result can be provided to the user despite of the occurrence of anomaly.

(Modification of Analysis Unit)

Figure 25A:
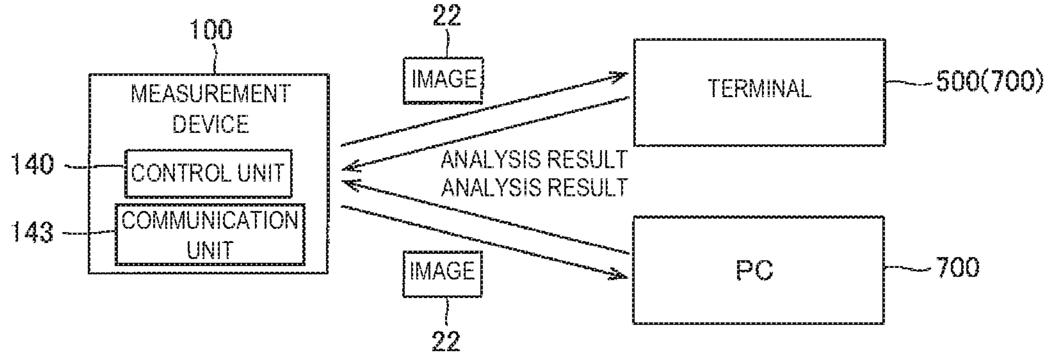
FIGS. 25A and 25B are diagrams illustrating examples in which image analysis is performed by an external analysis device of a measurement device.
Figure 25B:
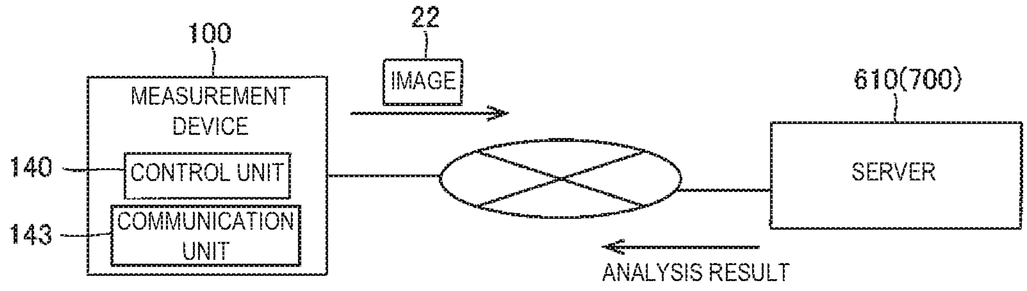

Although FIG. 6 illustrates the example in which the measurement device 100 includes the analysis unit 142 that performs image analysis, FIGS. 25A and 25B illustrate an example in which image analysis is performed by an external analysis device 700 of the measurement device 100.

In an exemplary configuration illustrated in FIG. 25A, the measurement device 100 is connected with an external personal computer (PC) or the terminal 500 through the communication unit 143. The external PC or the terminal 500 executes an analysis computer program to function as the analysis device 700 that performs image analysis. In FIG. 25A, the measurement device 100 and the analysis device 700 are connected with each other in a wired or wireless manner. The control unit 140 of the measurement device 100 transmits the captured image 22 to the external analysis device 700 through the communication unit 143. The analysis device 700 analyzes the received image 22. Processing executed by the analysis device 700 is same as that by the above-described analysis unit 142. The analysis device 700 transmits a result of the analysis to the measurement device 100.

In the exemplary configuration illustrated in FIG. 25B, the measurement device 100 can access, through the communication unit 143, to a server 610 connected with a network. The external server 610 functions as the analysis device 700 performs that image analysis. The server 610 is an image analysis server, but image analysis may be performed by the measurement result management server 600 (refer to FIG. 7) or the reagent and calibration curve management server 650 (refer to FIG. 7) as described above. In FIG. 25B, the control unit 140 of the measurement device 100 causes the communication unit 143 to transmit the captured image 22 to the external analysis device 700 through the network. The analysis device 700 analyzes the received image 22. Processing executed by the analysis device 700 is same as that by the above-described analysis unit 142. The analysis device 700 transmits analysis result information to the measurement device 100.

In each exemplary configuration illustrated in FIG. 25A or 25B, when no analysis unit that performs image analysis is provided due to constraint on the structure of the small-sized measurement device 100 for PoC testing, image analysis can be performed by using the external analysis device 700. Thus, the state of the monitoring target MT can be checked based on an analysis result of the image 22 of the monitoring target MT when no image analysis is performed by the measurement device 100.

(Modification of Image Capturing Unit and Image Capturing Range)

Figure 26:
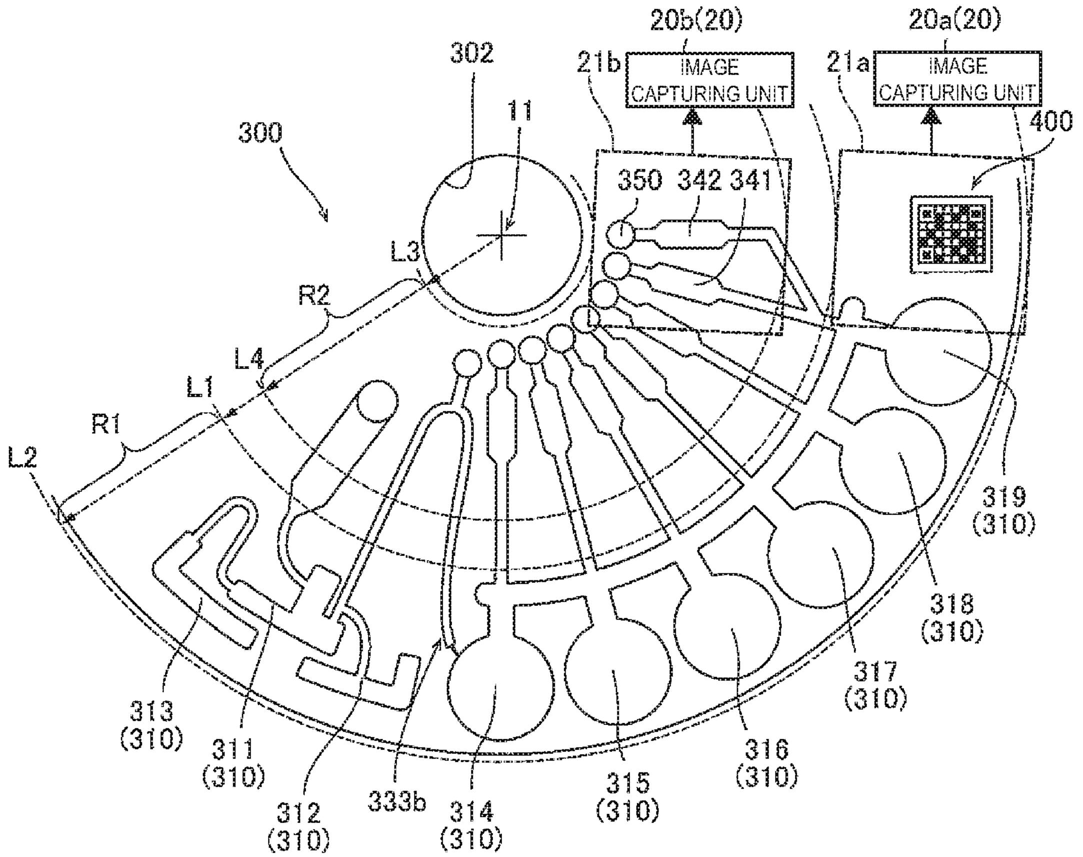
FIG. 26 is a diagram illustrating an image capturing unit and an image capturing range according to a first modification.

Although FIG. 10 illustrates the example in which the single image capturing unit 20 and the single image capturing range 21 are provided, FIG. 26 illustrates an example in which a plurality of image capturing ranges 21 are provided by a plurality of image capturing units 20. In FIG. 26, the measurement device 100 includes two image capturing units 20*a* and 20*b*. The two image capturing units 20*a* and 20*b* are disposed side by side in the radial direction. Accordingly, in FIG. 26, two image capturing ranges 21*a* and 21*b* are set on the surface of the cartridge 300 by the two image capturing units 20*a* and 20*b*, respectively. The image capturing range 21*a* provided by the image capturing unit 20*a* on the outer side in the radial direction is set at a position same as that in the example illustrated in FIG. 10. The image capturing range 21*b* provided by the image capturing unit 20*b* on the inner side in the radial direction is set to be a range R2 in which the distance from the rotational shaft 11 is between L3 and L4 inclusive (L4<L1 and L3<L4) so that the range includes the movement path of the housing unit 341 housing the reagent. In this case, the monitoring target MT includes the housing unit 341 of the reagent and the sealing body 350.

Figure 27:
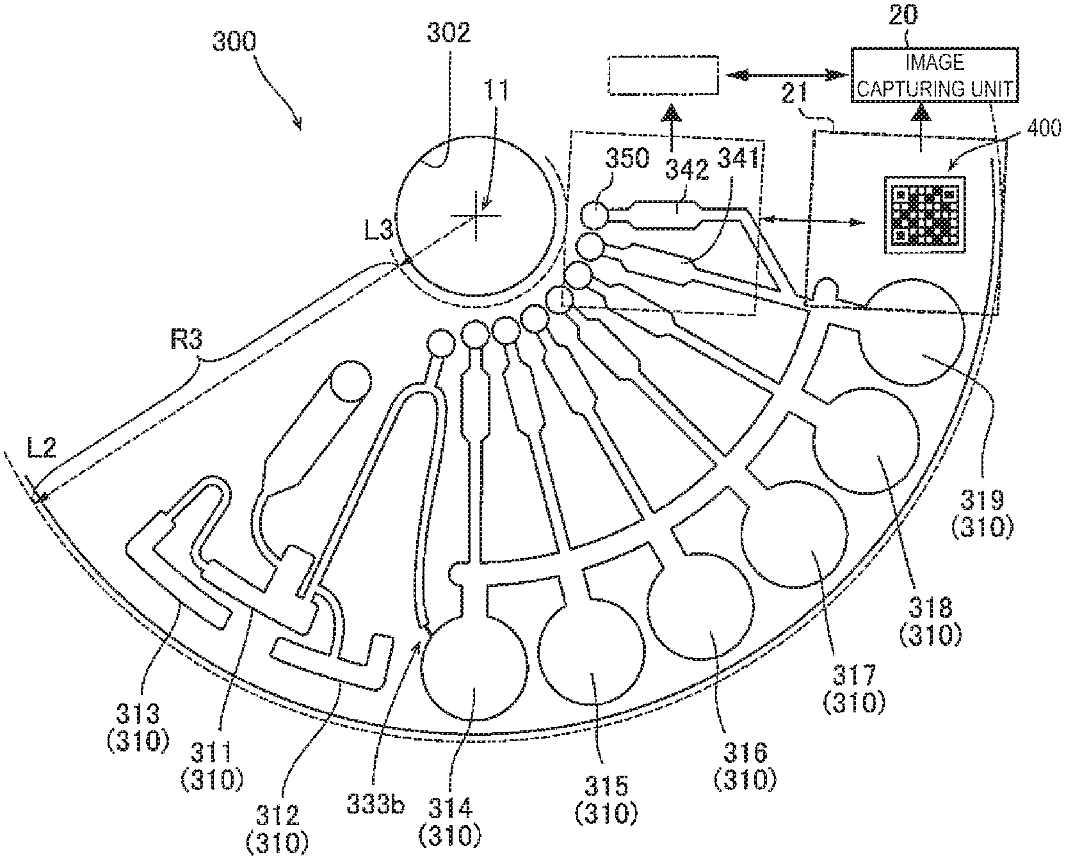
FIG. 27 is a diagram illustrating an image capturing unit and an image capturing range according to a second modification.

In an example illustrated in FIG. 27, the image capturing unit 20 is movable in the radial direction. The image capturing unit 20 is moved in the radial direction by combination of a drive source such as a motor, and a linear movement mechanism such as a screw shaft. Accordingly, the image capturing range 21 can be moved to an optional position in a range R3 in which the distance from the rotational shaft 11 is between L3 and L2 inclusive. In this case, the image 22 of the monitoring target MT can be acquired by the one image capturing unit 20 in a range equivalent to that of the configuration including the two image capturing units 20 as illustrated in FIG. 26.

The image capturing unit 20 may be, for example, a line sensor extending straight in the radial direction. In this case, the image capturing range 21 extends straight in the radial direction and has a narrow width. The image 22 of the monitoring target MT is formed when the monitoring target MT passes through the image capturing range 21 as the cartridge 300 is rotated (scanned) so that the monitoring target MT moves across the image capturing range 21.

(Modification of Identifier)

Although FIG. 10 illustrates the example in which information is read through image capturing of the identifier 400 by the image capturing unit 20, a reading unit dedicated to reading of the identifier 400 may be additionally provided. In this case, the identifier 400 may be integrated with the cartridge 300 or may be provided separately from the cartridge 300 and attached to the cartridge 300.

When the reading unit is provided, the identifier 400 may be an information storage medium from which information can be read by a method other than image reading. The identifier 400 may be, for example, an RF tag from which reading is possible in a non-contact manner by near field communication, a magnetic storage medium such as a magnetic stripe card, or an electronic storage medium such as a flash memory. When the identifier 400 is an RF tag, the reading unit is a reader device that uses near field communication. For example, when the identifier 400 is a magnetic storage medium such as a magnetic stripe card, the reading unit is a magnetic reader device. For example, when the identifier 400 is an electronic storage medium such as a flash memory, the reading unit is an interface to which the electronic storage medium can be connected to perform information reading.

(Modification of Cartridge)

Figure 28:
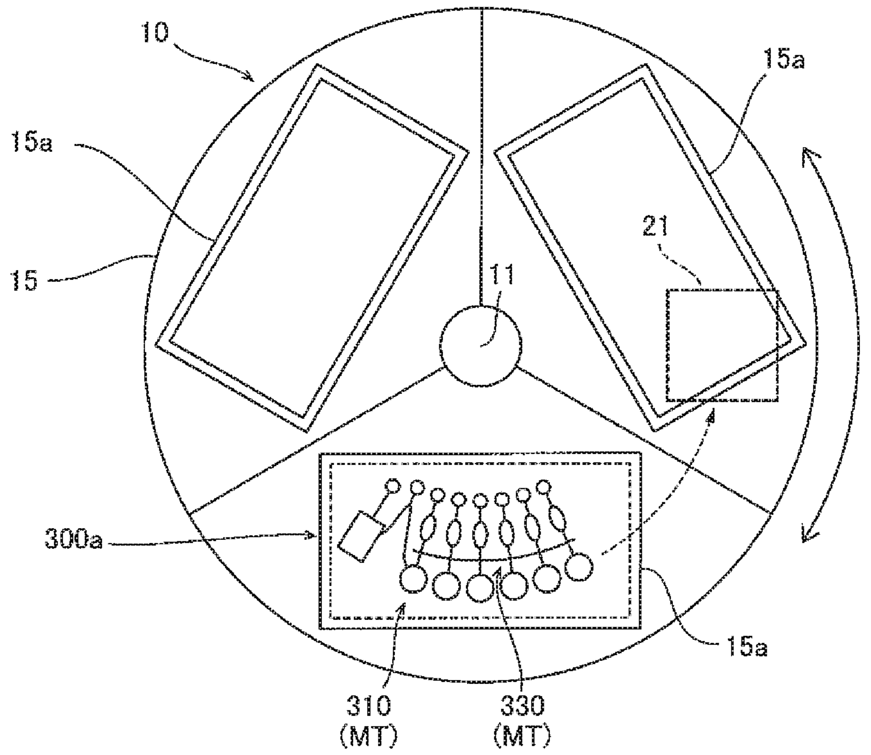
FIG. 28 is a diagram illustrating a cartridge according to a modification.
Figure 29:
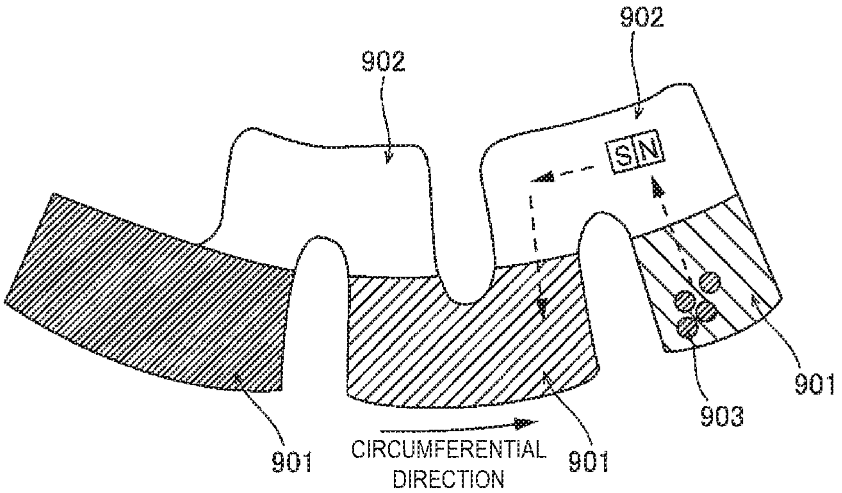
FIG. 29 is a diagram illustrating a conventional technology.

Although FIG. 10 illustrates the example in which the disk-shaped cartridge 300 is used, FIG. 28 illustrates an example in which a rectangular plate cartridge 300*a* is used in place of the disk-shaped cartridge 300. The other configuration is same as the specific exemplary configuration according to the above-described embodiment.

The support member 15 includes a rectangular disposition region 15*a* corresponding to the cartridge 300*a*. FIG. 28 illustrates an exemplary configuration in which the three disposition regions 15*a* are provided in the circumferential direction of the disk-shaped support member 15. The cartridge 300*a* is provided with housing units, chambers, and paths same as those of the cartridge 300 illustrated in FIG. 10. Similarly to FIG. 10, the cartridge 300 may be provided with the identifier 400.

In FIG. 28, too, in the cartridge 300*a* installed in each disposition region 15*a*, the monitoring target MT such as each chamber 310 or the path 330 is rotated on a movement path in a circular shape about the rotational shaft 11. Thus, when the image capturing range 21 is set on the movement path, each cartridge 300*a* can be rotated about the rotational shaft 11 to dispose the monitoring target MT in the common image capturing range 21. The cartridges 300*a* disposed in the three disposition regions 15*a* may be prepared for measurement of an identical measurement item, or may be prepared for measurement of measurement items different from each other. In the example illustrated in FIG. 28, the measurement device 100 can perform the measurement operation simultaneously in parallel on the three cartridges 300*a* at maximum.

Embodiments disclosed herein are merely exemplary in any way and should not limit the present invention. The scope of the present invention is defined by the claims, not by the above description of the embodiments, and includes all modifications in meanings and ranges equivalent to the claims.

The invention claimed is:

1. A measurement method for measuring a detection material contained in a sample by using a cartridge comprising: chambers each capable of housing at least one of the detection material and a reagent; and a path through which the detection material is transferred between a first chamber and a second chamber of the chambers, the method comprising:

positioning the first chamber to an image capturing range by rotating the cartridge about a rotational shaft;

capturing, by an image capturing unit, an image of the first chamber that is positioned in the image capturing range by rotating the cartridge;

positioning the second chamber to the image capturing range by rotating the cartridge about the rotational shaft;

capturing, by the image capturing unit, an image of the second chamber that is positioned in the image capturing range by rotating the cartridge; and measuring, by a measurement unit which is different from the image capturing unit, the detection material in at least one of the chambers, which is positioned at a measurement position by rotating the cartridge.

2. The measurement method according to claim 1, wherein measuring the detection material comprises measuring light attributable to the detection material moved to the measurement position.

3. The measurement method according to claim 1, wherein the image is captured in a direction facing a surface of the cartridge, and the image capturing range is disposed on a circumferential movement path on which a monitoring target moves with rotation.

4. The measurement method according to claim 3, wherein the image capturing range is disposed at a distance between a first distance and a second distance greater than the first distance, inclusive from the rotational shaft, and in the cartridge, the monitoring target is provided in a range at a distance between the first distance and the second distance, inclusive, from the rotational shaft.

5. The measurement method according to claim 3, wherein the monitoring target comprises a plurality of monitoring targets, and in the cartridge, the plurality of monitoring targets is disposed in an arc shape having a substantially equal distance from the rotational shaft.

6. The measurement method according to claim 1, wherein the image capturing range is fixed at least in measurement processing.

7. The measurement method according to claim 1, wherein the image capturing unit is fixed to a lid that is configured to cover the cartridge and is capable of opening and closing.

8. The measurement method according to claim 1, wherein the chambers comprise:

a monitoring target comprising the first chamber and the path.

9. The measurement method according to claim 8, further comprising:

acquiring, based on an area of liquid in the image of the first chamber, information on at least one of an amount of the sample in the first chamber and an amount of the reagent in the first chamber.

10. The measurement method according to claim 8, wherein the detection material and the reagent are agitated in the first chamber by rotating of the cartridge, and the method further comprises acquiring, based on grayscale of the image of the first chamber, information on uniformity of mixing of the detection material and the reagent.

11. The measurement method according to claim 8, wherein the monitoring target comprises the first chamber and the second chamber, and the method further comprises acquiring, based on grayscale of the carrier carrying the detection material in the image of each of the first chamber and the second chamber, information on an amount of the carrier transferred from the first chamber to the second chamber.

12. The measurement method according to claim 8, wherein the chambers comprise a third chamber in which the sample is housed, and the monitoring target comprises the third chamber.

13. The measurement method according to claim 12, further comprising:

rotating the cartridge to separate a liquid component and a solid component contained in the sample in the third chamber, and acquiring, based on an area of the solid component in an image of the third chamber, information on at least one of a state of the separation and an amount of the solid component.

14. The measurement method according to claim 12, wherein the chambers comprise a fourth chamber in which an excessive amount of the sample left after a certain amount of the sample is housed in the third chamber is housed, the monitoring target comprises the fourth chamber, and the method further comprises acquiring, based on an image of the fourth chamber, information on a presence of the sample in the fourth chamber.

15. The measurement method according to claim 9, further comprising:

controlling, based on the acquired information, outputting of a measurement result obtained through the measurement of the detection material.

16. The measurement method according to claim 15, wherein, in a condition in which the acquired information indicates anomaly:

measurement processing is stopped without outputting the measurement result;

the measurement result is output with additional information indicating an occurrence of the anomaly; or the measurement result is corrected and output.

17. The measurement method according to claim 1, wherein the cartridge comprises an identifier in which information is recorded, the method further comprises:

moving the identifier into the image capturing range by rotating of the cartridge, and reading the information recorded in the identifier by capturing an image of the identifier.

18. The measurement method according to claim 17, wherein the information recorded in the identifier comprises at least one of:

information that specifies a measurement item measurable by using the cartridge;

information on the reagent housed in the cartridge; and information that specifies the cartridge.

19. The measurement method according to claim 5, further comprising:

moving each of the plurality of monitoring targets into the identical image capturing range by rotating the cartridge, and capturing the image of each of the plurality of monitoring targets.

20. A measurement method for measuring a detection material contained in a sample by using a cartridge comprising: chambers each capable of housing at least one of the detection material and a reagent; and a path through which the detection material is transferred between a first chamber and a second chamber of the chambers, the method comprising:

positioning the first chamber to an image capturing range by rotating the cartridge about a rotational shaft;

capturing, by an image capturing unit an image of the first chamber that is positioned in the image capturing range by rotating the cartridge;

positioning the second chamber to the image capturing range by rotating the cartridge about the rotational shaft;

capturing, by the image capturing unit, an image of the second chamber that is positioned in the image capturing range by rotating the cartridge; and measuring, by a measurement unit which is different from the image capturing unit, the detection material in at least one of the chambers, which is positioned at a measurement position by rotating the cartridge; and checking whether a measurement processing is appropriately performed or whether anomaly occurs in the measurement processing based on the captured images of the first chamber and the second chamber.

* * * * *